United States Patent
McConnell et al.

(10) Patent No.: US 9,671,415 B2
(45) Date of Patent: Jun. 6, 2017

(54) IMMUNOASSAY FOR PYRROLIDINOPHENONES

(71) Applicant: RANDOX LABORATORIES LIMITED, Crumlin (GB)

(72) Inventors: Ivan McConnell, Crumlin (GB); Peter Fitzgerald, Crumlin (GB); Philip Lowry, Crumlin (GB); Elouard Benchikh, Crumlin (GB)

(73) Assignee: Randox Laboratories Limited, Crumlin, County Antrim (GB)

( * ) Notice: Subject to any disclaimer, the term of this patent is extended or adjusted under 35 U.S.C. 154(b) by 0 days.

(21) Appl. No.: 14/874,047

(22) Filed: Oct. 2, 2015

(65) Prior Publication Data

US 2016/0097783 A1   Apr. 7, 2016

(30) Foreign Application Priority Data

Oct. 2, 2014   (GB) .................................. 1417447.8

(51) Int. Cl.
*G01N 33/94* (2006.01)
*C07K 16/44* (2006.01)

(52) U.S. Cl.
CPC ............. *G01N 33/94* (2013.01); *C07K 16/44* (2013.01); *G01N 33/946* (2013.01); *C07K 2317/33* (2013.01)

(58) Field of Classification Search
CPC .... C07K 16/44; C07K 2317/33; G01N 33/94; G01N 33/946
See application file for complete search history.

(56) References Cited

U.S. PATENT DOCUMENTS

| 2008/0125579 | A1 | 5/2008 | Owens et al. | |
| 2008/0234498 | A1* | 9/2008 | Butler | C07D 207/325 548/570 |
| 2013/0210167 | A1* | 8/2013 | Benchikh | C07D 405/06 436/501 |

FOREIGN PATENT DOCUMENTS

| EP | 2442110 A1 | 4/2012 |
| EP | 2626358 B1 | 9/2015 |

OTHER PUBLICATIONS

Rao, "Immunology," 2005.*

(Continued)

*Primary Examiner* — Galina Yakovleva
(74) *Attorney, Agent, or Firm* — Faegre Baker Daniels LLP

(57) ABSTRACT

The current invention provides an improved immunoassay for the detection and determination of pyrrolidinophenone based designer drugs in hair and biological fluids (urine, blood, and oral fluid). The generic immunoassay is underpinned by novel, sub-family-specific antibodies, which display surprising sensitivity. The invention further describes substrates comprising an antibody that is specific to compounds of the pyrrolidinophenone family. Also described are the novel immunogens from which the antibodies are derived and kits incorporating the antibodies of the current invention.

7 Claims, 4 Drawing Sheets

(56) References Cited

OTHER PUBLICATIONS

Alpha Diagnostic International, Product Data Sheet, Cat# 700-101, "Keyhole limpet hemocyanin (KLH, hemocyanin) coated ELISA plates," posted on Internet Apr. 10, 2013.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Fitzgerald, Stephen P., Lamont, John V., McConnell, Robert I., Benchikh, El O., "Development of a High-Throughput Automated Analyzer Using Biochip Array Technology," Clinical Chemistry 51:7, 1165-1176, Apr. 19, 2005, Crumlin, County Antrim, United Kingdom.
Marinetti, Laureen J. and Antonides, Heather M., "Analysis of Synthetic Cathinones Commonly Found in Bath Salts in Human Performance and Postmortem Toxicology: Method Development, Drug Distribution and Interpretation of Results," Journal of Analytical Toxicology 2013;1-12, Advance Access, published Jan. 29, 2013, Montgomery County Coroner's Office (MCCO)/ Miami Valley Regional Crime Laboratory, Dayton, Ohio.
Taylor & Francis Ltd., Edited by Professor Brian Law, Zeneca Pharmaceuticals, UK, "Immunoassay A Practical Guide," published in the Taylor & Francis e-Library, 2005, United Kingdom.
NMS Labs, "New Bath Salts: Popular, Deadly and Now Detectable," nmslabs.com; Jul. 2013.
Sauer, Christoph, Peters, Frank T., Haas, Claudia, Meyer, Markus R., Fritschi, Giselher, Mauerer, Hans H., "New designer drug α-pyrrolidinovalerophenone (PVP): studies on its metabolism and toxicological detection in rat urine using gas chromatographic/mass spectrometric techniques," Journal of Mass Spectrometry, 2009, 44, 952-964, published online in Wiley Intersciences Mar. 5, 2009.
Search Report in GB Patent Application No. GB1417447.8, Jun. 16, 2015.
Kriikku, Pirkko, et al., "New designer drug of abuse: 3,4-Methylenedioxypyrovalerone (MDPV). Findings from apprehended drivers in Finland", Forensic Science International, 2011, vol. 210, pp. 195-200.
Brandt, S. et al., "Analysis of second-generation 'legal highs' in the UK: Initial findings", Drug Testing and Analysis, 2, pp. 377-382, 2010.
Randox, Product Brochure, Cat# PVP10048, "Enzyme-Linked Immunosorbent Assay," revised Jun. 18, 2015.
Strano-Rossi, S. et al., "Toxicological determination and in vitro metabolism of the designer drug methylenedioxypyrovalerone (MPDV) by gas chromatography/mass spectrometry and liquid chromatography/quadrupole time-of-flight mass spectrometry", Rapid Communications in Mass Spectrometry, 24, pp. 2706-2714, 2010.
Yohannan, J. et al., "The Characterization of 3,4-Methylenedioxypyrovalerone (MDPV)", Microgram Journal, vol. 7, No. 1, pp. 12-15, 2010.

* cited by examiner 6
(Hapten-2)

Hapten-1

Hapten-2

IMMUNOASSAY FOR PYRROLIDINOPHENONES

RELATED APPLICATIONS

The instant application claims the benefit of priority under 35 USC §119 to United Kingdom Application No. 1417447.8, entitled "Improved Immunoassays for pyrrolidinophenones", filed Oct. 2, 2014, the entire contents of which are incorporated herein by reference in their entirety.

BACKGROUND

The synthetic cathinones are a class of drugs which have risen to popularity through their use as synthetic stimulants. Just as the synthetic cannabinoids have been marketed under the guise of "incense", synthetic cathinones are commonly sold as "bath salts" or occasionally plant food, insect repellent, pond cleaner and vacuum freshener, all of which are often labelled as "not for human consumption". They are available online and from local suppliers under a variety of names including Ivory wave, Cloud nine, Scarface, Vanilla sky, White lightning, Blizzard, Snow leopard, Red dove, Hurricane Charlie, Gravel and Blue silk. Synthetic cathinones and their derivatives are related to the naturally occurring alkaloid cathinone which is found in the Khat plant, *Catha edulis* and has mildly stimulating properties.

Synthetic cathinones are used to mimic the effects of cocaine and amphetamines and physical side-effects of these drugs include tachycardia, hypertension, arrhythmias, and seizures. They are also associated with a range of behavioural or mental-state effects including panic attacks, anxiety, paranoia, hallucinations and aggressive or violent behaviour. A number of deaths have also been linked to the use of "bath salts" (Marinetti & Antonides, 2013).

Since their rise as recreational drugs, governments around the world have taken actions to control synthetic cathinones. For example, in 2010, the UK government ordered a broad substituted cathinone ban in response to growing reports of mephedrone use. On 21 Oct. 2011, the Drug Enforcement Administration in the United States (DEA) finalized the temporary scheduling of mephedrone, methylone and MDPV (3',4'-Methylenedioxy-α-pyrrolidopentiophenone) into schedule I under the Controlled Substances Act; in July 2012, this was made permanent.

Following the illegalization of these compounds, a second generation of synthetic cathinones emerged including alpha-pyrrolidinopentiophenone (RS)-1-phenyl-2-(1-pyrrolidinyl)-1-pentanone, hereinafter referred to as α-PVP. Between April and June 2013, α-PVP was the most prevalent drug in samples which tested positive on NMS labs Bath Salts Panel (NMS labs, 2013). In some countries, these fell under current legislation as analogues of banned compounds but in others, such as the USA, new bans had to be put in place. On Jan. 28 2014, the DEA temporarily listed α-PVP along with 9 other synthetic cathinones as Schedule I controlled substances; 4-methyl-N-ethylcathinone ("4-MEC"); 4-methyl-alphapyrrolidinopropiophenone ("4-MePPP"); 1-(1,3-benzodioxol-5-yl)-2-(methylamino)butan-1-one ("butylone"); 2-(methylamino)-1-phenylpentan-1-one ("pentedrone"); 1-(1,3-benzodioxol-5-yl)-2-(methylamino)pentan-1-one ("pentylone"); 4-fluoro-N-methylcathinone ("4-FMC"); 3-fluoro-N-methylcathinone ("3-FMC"); 1-(naphthalen-2-yl)-2-(pyrrolidin-1-yl)pentan-1-one ("naphyrone"); and alpha-pyrrolidinobutiophenone ("α-PBP").

A study on the metabolism of α-PVP in rats (Sauer et al., 2009) suggested the following routes; hydroxylation of the side chain followed by dehydrogenation to the corresponding ketone; hydrogenation of the 2'-position of the pyrrolidine ring followed by dehydrogenation to the corresponding lactam; degradation of the pyrrolidine ring to the corresponding primary amine; hydroxylation of the phenyl ring, most probably in the 4' position; and ring opening of the pyrrolidine ring to the corresponding carboxylic acid.

Current analytical methods tend to use mass-spectrometry (MS) in conjunction with gas chromatography (GC) or liquid chromatography (LC) (Sauer et. al, 2009; Marinetti & Antonides, 2013). A disadvantage of such methods of detection is that they require expensive equipment and highly trained staff. On the other hand, immunoassays are known in the art as relatively cost effective, simplistic and rapid alternatives to MS based analysis. European patent number EP2626358 provides an immunoassay for detecting pyrrolidinophenones including MDPBP (3',4'-Methylenedioxy-α-pyrrolinobutiophenone), naphyrone, MPVP (4-Methyl-α-pyrrolidinopentiophenone), MDPV and MDPPP (3',4'-Methylenedioxy-α-pyrrolinopropiophenone) with very low cross-reactivity to α-PVP. Antibodies in EP2626358 are characterised having an $IC_{50}$ value of greater than 20 ng/ml for each of the pyrrolidinophenones to which cross-reactivity is shown. There remains a need for an improved generic immunoassay which is not only more sensitive to the range of pyrrolidinophenone based compounds currently found in seized drugs, but that can also detect analogues and derivatives which may make their way onto the market in the future so as to enable improvements in the forensic, toxicological and clinical analysis of the intake of these ever evolving designer drugs.

REFERENCES

Sauer, C. et al. J. Mass. Spectrom. (2009); 44(6), 952-964.
Marinetti, L. J and Antonides, H. M. J. Anal. Toxicol. (2013); 37(3), 135-146.
Immunoassay: A practical guide, by Brian Law, Taylor and Francis Ltd, ISBN 0-203-48349-9.
FitzGerald, S. P. et al. Clin. Chem. (2005); 51(7), 1165-1176.
http://www.nmslabs.com/uploads/PDF/Bath_Salts_July_2013_PDF_letter.pdf

SUMMARY OF INVENTION

Figure 1:
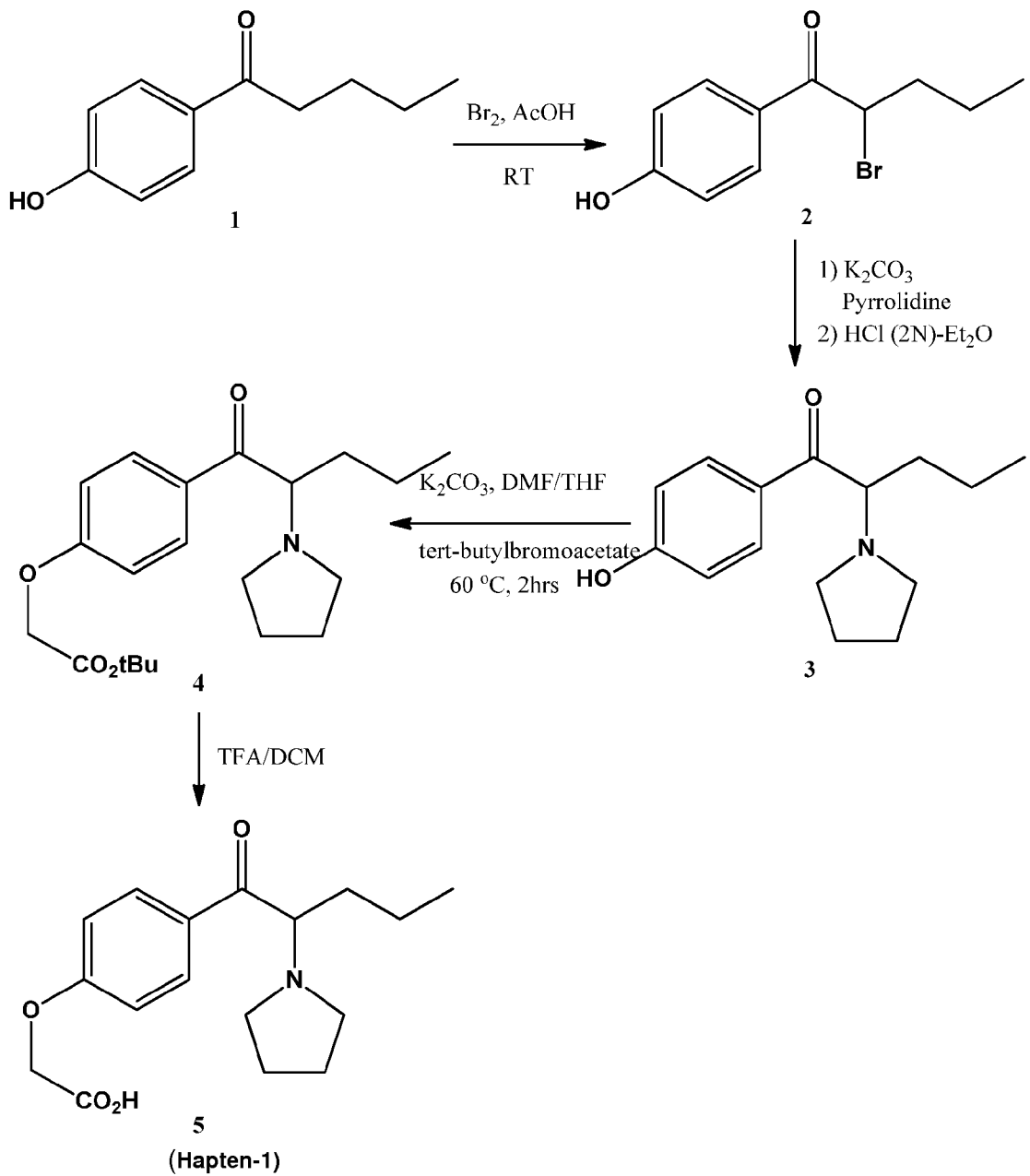
FIG. 1 Synthesis of 2-[4-(2-(pyrrolidin-1-yl)pentanoyl)phenoxy]acetic acid (PVP 4-CME) 5 (Hapten-1).

Described herein is an improved immunoassay for the detection and determination of pyrrolidinophenone based designer drugs. These designer drugs can be tested from samples or solutions of products that have been sold, shipped or transported. These designer drugs can also be tested in hair and biological fluids (urine, blood, and oral fluid) of a subject. The immunoassay is underpinned by novel, sub-family-specific antibodies which display surprising sensitivity. The invention further describes substrates comprising an antibody that is specific to compounds of the pyrrolidinophenone family. Also described are the novel immunogens from which the antibodies are derived and kits incorporating the antibodies of the current invention.

In one embodiment the present invention is an immunogen of structure I:

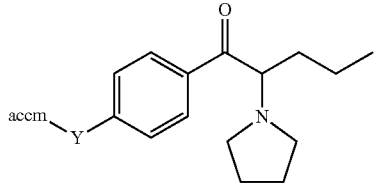

Structure I wherein: Y is a crosslinking group; and accm is an antigenicity-conferring carrier material. In another embodiment, wherein: Y is -(A)$_n$-B-D-; A is a functional group or heteroatom enabling attachment of the crosslinking group to the phenyl ring; B is an optionally substituted $C_1$-$C_{10}$, alkylene moiety optionally incorporating a cycloalkyl and/or a heterocyclic moiety; D is a functional group or heteroatom enabling attachment of the crosslinking group to the antigenicity-conferring carrier material (accm); and n=0 or 1. In one embodiment, B is an optionally substituted $C_1$-$C_6$ alkylene moiety. In another embodiment, A is —O—, —NH— or —S—; D is —C(O)—, —NH—, —C≡, —C(O)—NH—, —NHC(O)—, —C(O)—NH—CH(COOH)—CH$_2$—CH$_2$—S—, —C(O)—NHCH(COOH)—CH$_2$—CH$_2$—S-maleimide-, or —S—; and n=1.

In another embodiment the present invention is an antibody that binds to an epitope of structure II:

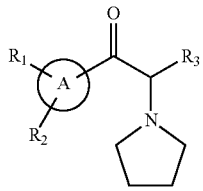

Structure II wherein: A is aryl; $R_3$ is $C_1$-$C_6$ alkyl; and each $R_1$ and $R_2$ is independently —H, $C_1$-$C_4$ alkyl, $C_1$-$C_4$ alkoxy, hydroxy substituted $C_1$-$C_4$ alkyl, carboxy, halo, or hydroxy; or $R_1$ and $R_2$ join together to form an optionally substituted:

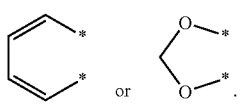 [SMILES: */C=C\C=C/* ; *OCO*]

In another embodiment, the present invention is a method of detecting or determining a compound comprising structure II:

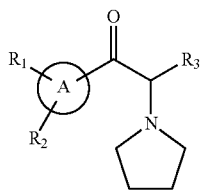

Structure II wherein: A is aryl; $R_3$ is $C_1$-$C_6$ alkyl; and each $R_1$ and $R_2$ are independently —H, $C_1$-$C_4$ alkyl, $C_1$-$C_4$ alkoxy, hydroxy substituted $C_1$-$C_4$ alkyl, carboxy, halo, or hydroxy; or $R_1$ and $R_2$ join together to form an optionally substituted:

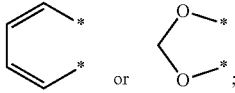 [SMILES: */C=C\C=C/* ; *OCO*]

in a sample, the method comprising: i) contacting the sample with a detecting agent and an antibody, wherein the antibody is raisable from an immunogen of structure I:

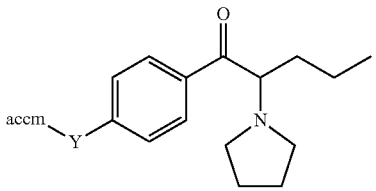

Structure I wherein: Y is a crosslinking group; and accm is an antigenicity-conferring carrier material; wherein both the compound and the detecting agent bind to the antibody; and ii) detecting or determining the amount of detecting agent bound to the antibody. In one embodiment A is phenyl or thiophene.

In one embodiment the present invention is a kit comprising an antibody described herein.

DETAILED DESCRIPTION OF THE INVENTION

Unless otherwise stated, technical terms as used herein are used according to the conventional usage as known to those skilled in the art.

The chemical structures of the pyrrolidinophenone compounds referred to herein are given in Table 3.

The invention describes a method of detecting or determining pyrrolidinophenone compounds in a solution or an in vitro sample from a subject comprising; contacting the solution or sample with one or more detecting agents and one or more antibodies; wherein both the compound and the detecting agent bind to the antibody; detecting, or determining the quantity of, the one or more detecting agents; and determining or deducing (optionally from calibrators) the presence of, or the amount of, pyrrolidinophenone compounds in the sample or solution, wherein the one or more antibodies is, optionally, raisable from an immunogen of structure I, or Immunogen-1A or -1B.

The term "hapten" as used herein, describes a pre-immunogenic molecule that stimulates antibody production only when linked to a larger carrier molecule. For the purposes of this patent application, "linked" is synonymous with bound, attached, conjugated, crosslinked, coupled, or chemically synthesised to. This larger carrier molecule can be referred to as an antigenicity-conferring carrier material (accm). Once the hapten is linked to the accm, it forms the immunogen.

The term "immunogen" as used herein, describes an entity that induces an immune response such as production of antibodies or a T-cell response in a host animal.

The term "carrier molecule" refers to a molecule to which a hapten or antigen can be linked to impart immunogenic properties to the hapten or antigen. The term "carrier molecule" may be used interchangeably with the terms "carrier", "immunogenicity conferring carrier molecule" and "antigenicity conferring carrier material".

The accm can be any material that makes all or part of the hapten susceptible to antibody recognition and binding. For example, the accm can be a protein, a protein fragment, a synthetic polypeptide or a semi-synthetic polypeptide. Alternatively, the accm comprises synthetic poly (amino acids) having a sufficient number of available amino groups, such as lysine. Further alternatively, the accm is selected from synthetic or natural polymeric materials bearing reactive functional groups. Still further alternatively, the accm is selected from carbohydrates, yeasts and polysaccharides. Illustrative examples of useful antigenicity-conferring carrier materials are bovine serum albumin (BSA), egg ovalbumin (OVA), bovine gamma globulin (BGG), bovine thyroglobulin (BTG), keyhole limpet haemocyanin (KLH) etc. Optionally, the accm is selected from KLH or BSA. Further optionally, the, the accm is KLH.

It will be understood that the haptens of the current invention may be attached to the antigenicity-conferring carrier material (accm) via a crosslinking group. The crosslinking group may be any conventional cross linking group conventionally used in this field. The crosslinking group is ideally a functionalised linking group joining the accm to the hapten. The term "crosslinking group" as used herein is any bifunctional molecule able to covalently join the hapten element to an immunogenicity conferring carrier material. A suitable crosslinking group to link with alternative carrier materials is maleimide, or a maleimide derivative, for example when BTG-maleimide is used to conjugate with the hapten via a cysteine residue. Other cross-linking groups which could also couple this group on the cysteine include haloacetyls and pyridyldisulfides. Either Lys residue, or the Glu residue (C-terminal) may alternatively be used to conjugate to a carrier material, optionally via a cross-linking group, to form an immunogen. For example, a primary amine group on the side chain of lysine (Lys) could be coupled using a crosslinking group selected from N-hydroxysuccinimide esters, imidoesters, PFP esters or hydroxymethyl phosphine. As another example, glutamic acid (Glu) could be coupled using a carbodiimide crosslinking group: 1-Ethyl-3-(3-dimethylaminopropyl)carbodiimide EDC or N,N'-Dicyclohexylcarbodiimide (DCC). In one embodiment, the cross-linking group may comprise, or consist of, a carboxyl, dithiopyridyl, maleimidyl, amino, hydroxyl, thiol and aldehyde moiety. In another embodiment, the cross-linking group may comprise, or consist of, a carboxyl moiety. The cross-linking group is well known to the skilled person in immunogen synthesis.

According to a first aspect of the invention, there is provided an immunogen having the general formula:

Structure I

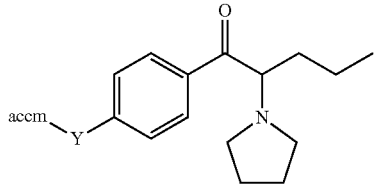

In one embodiment, Y is a crosslinking group and accm is an antigenicity-conferring carrier material.

In one embodiment, Y is -(A)$_n$-B-D, in which B is an optionally substituted $C_1$-$C_{10}$ alkylene moiety or an optionally substituted $C_1$-$C_6$ alkylene moiety, wherein the alkylene moieties optionally incorporate (i.e., wherein one or more methylene group of the alkylene is optionally replaced by) a cycloalkyl and/or a heterocyclic moiety; n=0 or 1 and A is a functional group or heteroatom enabling, when present, attachment of the crosslinking group to the phenyl ring and D is a functional group or heteroatom enabling attachment of the crosslinking group to the antigenicity-conferring carrier material.

The term "functional group" is a standard phrase in the chemistry field and refers to a reactive group such as an amine, ketone, ether, thioether, amide, the double bond of an alkene, thiol, ester, carboxylic acid or aldehyde. In one embodiment, A is —O—, —S— or —N—. In another embodiment, A is —O—, —S— or —NH—. In one embodiment A is —O—. The substituents of the alkylene chain of B can either be incorporated off, within or at the end of the alkylene chain. Usually the substituents will be functional groups at the end of the alkylene chain which have participated in chemical bonding in order to form a link between the pyrrolidinophenone structure and the carrier material. The conjugation of the accm to Y can be facilitated by, for example, the presence of a carboxylic acid or an ester thereof, an aldehyde, an amino group, a maleimide, a halocarboxylic acid or an ester thereof, a dithiopyridyl moiety, a vinylsulphone moiety, a thiocarboxylic acid or an ester thereof. In one embodiment, D is carbonyl, amino, thiol, or diazo. In another embodiment, D is —C(O)—, —NH—, —C=, —C(O)—NH—, —C(O)NH—CH(COOH)—CH$_2$—CH$_2$—S—, —C(O)—NHCH(COOH)—CH$_2$—CH$_2$—S-maleimide-, or —S—. In one embodiment D is —C(O)—, —NH—, —C(O)—NH—, or —NHC(O)—. In one embodiment D is —C(O)—. In a further embodiment, D is generated by reacting accm with B which is substituted with a terminal functional group selected from the group consisting of maleimide, isothiocyanate and dithiopyridine.

For the avoidance of doubt in, for example, the formation of an immunogen from Hapten-2: the ring structure opens at the thioamide bond and the free —SH group thus formed attaches to accm or label, i.e. forming —C(O)—NHCH(COOH)—CH$_2$—CH$_2$—S-accm, so that D is —C(O)—NH—CH(COOH)—CH$_2$—CH$_2$—S—. In one embodiment n=1. In one embodiment, A is —O—, D is —C(O)—, —C(O)NH—CH(COOH)—CH$_2$—CH$_2$—S—, —C(O)—NHCH(COOH)—CH$_2$—CH$_2$—S-maleimide-B is a methylene, and n is 1.

An example of an immunogen of the current invention is 2-(4-(2-(pyrrolidin-1-yl)pentanoyl)phenoxy)acetic acid (Hapten-1) conjugated to an antigenicity conferring carrier molecule selected from KLH, BSA, BTG, BGG or OVA. Preparation of immunogens of the current invention are shown in Examples 6 and 7. In these reactions, N-Hydroxysuccinimide (NHS) plus 1-Ethyl-3-(3-dimethylaminopropyl)carbodiimide (EDC) are used to facilitate the cross-linking of the carboxyl group on Hapten-1 to an amide group on the accm.

A further aspect of the current invention is an antibody raisable from an immunogen described above. The term "antibody" as used herein refers to an immunoglobulin or immunoglobulin-like molecule. In one embodiment, the antibodies are polyclonal antibodies. However, the skilled person will understand that any type of immunoglobulin molecule or fragment thereof can be used, for example monoclonal antibodies, Fab fragments, scFv fragments and any other antigen binding fragments all of which fall within the scope of the current invention. The polyclonal antibodies may be produced by any method as known to those skilled in the art. Any suitable host animal may be used in the immunisation process including a mammalian animal for example, but not limited to, sheep, rabbit, mouse, guinea pig or horse. In addition, the antibodies may be in the form of polyclonal antisera.

The term "raisable" means that the antibody can be raised from an immunogen of the second aspect of the current invention but is not necessarily so raised. In this context, "raisable" includes, but is not limited to, "raised".

When used in reference to an antibody, the word "specific", "specifically" or "specificity" in the context of the current invention refers to the analyte or analytes that are preferably bound by the antibody, as gauged by a suitable metric such as the sensitivity and cross-reactivity. For purposes of comparison, one analyte with high cross-reactivity is generally given a value of 100%, with all other analytes accorded a value relative to this; in addition, as is known by one skilled in the art, for cross-reactivity to be of practical use the analyte specific antibody must display a high sensitivity as measured by a suitable metric such as the $IC_{50}$. The $IC_{50}$ is a commonly used indicator of antibody sensitivity for immunoassays. To enable an assay to be effectively applied in the field, an $IC_{50}$ of less than or about 20 ng/ml, less than or about 10 ng/ml, less than or about 5 ng/ml, or less than about 1 ng/ml or less than about 500 mg/ml for any individual analyte. Given the $IC_{50}$ of various analytes, their cross-reactivities, often represented as relative percentages, can be calculated.

The antibodies of the invention can be adsorbed on, or attached (covalently) to, a substrate. The substrate can be any substance or shape to which an antibody or antibody derivative can bind, either through chemical bonds (before which the substrate has to be chemically activated) or passive adsorption through mutual attraction of the substrate and antibody. Preferably, the antibodies are chemically bonded to the chemically activated substrate. The substrate can be, for example, plastic or magnetic beads, polystyrene microtitre plates (ELISA plates), planar nitrocellulose, a ceramic biochip or a biochip such as a plastic, glass or ceramic biochip surface-coated with a material that facilitates the immobilisation of the antibodies to the substrate. The antibodies or the substrate comprising the antibodies can be provided as discrete off-the-shelf reagents or be incorporated in a kit which optionally has other components such as a conjugate and/or calibrators.

The antibody raised to an immunogen of the current invention is capable of binding to an epitope of structure II, IIa or IIb:

Structure II

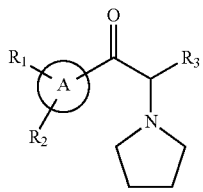

-continued

Structure IIa

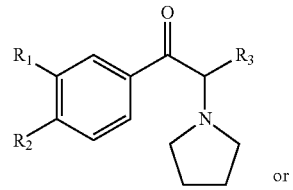

or

Structure IIb

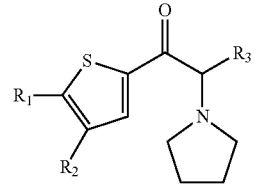

In one embodiment, the present invention is an antibody capable of binding to an epitope of structure II, IIa, or IIb or an epitope which is part of structure II, IIa, or IIb.

Ring A is aryl. In one embodiment, the antibody of the present invention can bind to structure II with any substituted or unsubstituted aromatic ring, in particular a 5 or 6 membered aromatic or heteroaromatic, substituted or unsubstituted ring. In one embodiment, ring A is a substituted or unsubstituted phenyl or a substituted or unsubstituted thiophene. $R_3$ is $C_1$-$C_6$ alkyl; or $C_2$-$C_6$ alkyl; each $R_1$ and $R_2$ are independently —H, $C_1$-$C_4$ alkyl, $C_1$-$C_4$ alkoxy, hydroxy substituted $C_1$-$C_4$ alkyl, carboxy or hydroxy; or each $R_1$ and $R_2$ are independently —H, $C_1$-$C_4$ alkyl, $C_1$-$C_4$ alkoxy, hydroxy substituted $C_1$-$C_4$ alkyl, carboxy, halo or hydroxy; or $R_1$ and $R_2$ join together to form an optionally substituted:

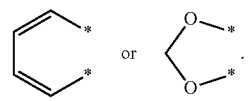 [SMILES: */C=C\C=C/* ; *OCO*]

In one embodiment, each $R_1$ and $R_2$ of structure II, IIa, and IIb are independently —H, methyl, or methoxy. In one embodiment, $R_3$ of structure II, IIa, and IIb is a $C_2$-$C_3$ alkyl. In one embodiment, $R_3$ of structure II, IIa, and IIb is a propyl. In one embodiment, each $R_1$ and $R_2$ of structure II, IIa, and IIb are independently —H or methyl or join together to form substituted:

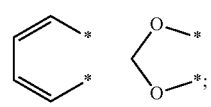

and $R_3$ is propyl.

In one embodiment, the antibody of the invention is capable of binding to at least one epitope of the compounds selected from the group comprising the molecules α-PVP, pyrovalerone, MDPV ((3',4'-methylenedioxy-α-pyrrolidopentiophenone), MDPBP (3',4'-Methylenedioxy-α-pyrrolinobutiophenone), naphyrone, and 4-methoxy-alpha-pyrrolidinopentiophenone (MOPVP). In another embodiment, the antibody of the invention is capable of binding to at least one epitope of the compounds selected from the group comprising the molecules α-PVP, pyrovalerone, MDPV (3',4'-methylenedioxy-α-pyrrolidopentiophenone), naphyrone and pyrrolidinopentothiophenone. In another embodiment, the antibody of the invention is capable of binding to at least one epitope of the compounds selected from the group comprising the molecules α-PVP, pyrovalerone and MDPV (3',4'-methylenedioxy-α-pyrrolidopentiophenone).

The term "able to bind to" or "capable of binding" as used herein means that under standard immunoassay conditions, for example as described in *Immunoassay: A practical guide* by Brian Law, Taylor and Francis Ltd (ISBN 0-203-48349-9), the antibodies will bind to said molecules. Due to inter-molecular attractive forces such as hydrogen bonding and van der Waal's forces, there is often a degree of binding or affinity between two molecules whatever their respective structures; the skilled person recognizes that no cross-reactivity or minimal cross-reactivity implies that, in the context of a working immunoassay, any binding or interaction between an antibody and non-target analytes is at such a low level that it does not compromise the integrity of the immunoassay i.e. false positives are avoided.

In an embodiment, the antibody has 100% cross-reactivity to α-PVP and greater than 100% cross-reactivity to one or more of pyrovalerone, MDPV, naphyrone and MOPVP. In an embodiment, the antibody has 100% cross-reactivity to α-PVP and greater than 100% cross-reactivity to pyrovalerone. In an embodiment, the antibody has 100% cross-reactivity to α-PVP and greater than 100% cross-reactivity to one or more of pyrovalerone and MDPV. In an embodiment, the antibody has 100% cross-reactivity to α-PVP and greater than 100% cross-reactivity to pyrovalerone and greater than 50% cross-reactivity to MDPV, α-pyrrolidinopentiothiophenone HCl, and naphyrone. In an embodiment, the antibody has 100% cross-reactivity to α-PVP and greater than 50% cross-reactivity to one or more of 4-methoxy-α-pyrrolidinopentiophenone, α-pyrrolidinopentiothiophenone HCl, and naphyrone. In one embodiment, the antibody has 100% cross-reactivity to α-PVP and less than 5% cross-reactivity to one or more of α-pyrrolidinopropiophenone, (+/−) 4'-methyl-α-pyrrolidinopropiophenone and 3,4-methylenedioxy-α-pyrrolidinopropiophenone (MDPPP). Optionally, the antibody has 100% cross-reactivity to α-PVP and greater than 100% cross-reactivity to pyrovalerone, MDPV, naphyrone and MOPVP, with less than 100% cross-reactivity to MDPBP. Optionally, the antibody has 100% cross-reactivity to α-PVP and greater than 100% cross-reactivity to one or more of pyrovalerone, MDPV, naphyrone and MOPVP, with less than 100% cross-reactivity to MDPBP. Optionally, the antibody has 100% cross-reactivity to α-PVP and greater than 100% cross-reactivity to one or both of pyrovalerone and MDPV and less than 5% cross-reactivity to one or more of α-pyrrolidinopropiophenone, (+/−) 4'-methyl-α-pyrrolidinopropiophenone and 3,4-methylenedioxy-α-pyrrolidinopropiophenone (MDPPP).

Additionally or alternatively, the antibody of the current invention may be characterised by its high sensitivity. In one embodiment, the antibody has an $IC_{50}$ of less than about 1 ng/ml, or less than about 0.5 ng/ml, for one or more of α-PVP, pyrovalerone, MDPV, MDPBP, naphyrone and MOPVP. In one embodiment, the antibody has an $IC_{50}$ of less than about 1 ng/ml, or less than about 0.5 ng/ml, for one of more of α-PVP, pyrovalerone, MDPV, α-pyrrolodinopentiothiophenone HCl, and naphyrone. In one embodiment, the antibody has an $IC_{50}$ of less than about 1 ng/ml, or less than about 0.5 ng/ml, for one of more of α-PVP, pyrovalerone and MDPV. In one embodiment, the antibody has an $IC_{50}$ of less than about 1 ng/ml, or less than about 0.5 ng/ml, for each of α-PVP, pyrovalerone and MDPV. In one embodiment, the antibody has an $IC_{50}$ of less than about 1 ng/ml, or less than about 0.5 ng/ml, for each of α-PVP, pyrovalerone, MDPV, α-pyrrolodinopentiothiophenone HCl, and naphyrone.

The use of the word "about" accounts for the expected minor variations in the measured $IC_{50}$ value which may arise during scientific analyses by different individuals when effecting the assay or from slight differences in assay equipment and reagents.

Another aspect of the invention is a kit comprising the antibody (or antibodies) of the invention. Optionally, the kit further comprises a conjugate, a calibrator, and instructions for use.

A further aspect of the invention is an immunoassay method of detecting or determining pyrrolidinophenone compounds or derivatives thereof in an in vitro sample from a subject or in a solution derived from a substance suspected to contain such compounds, the method comprising contacting the sample or solution with at least one detecting agent and at least one antibody of the invention; detecting or determining the detecting agent(s); and determining or deducing from a calibration curve the presence of, or amount of pyrrolidinophenone compounds in the sample or solution. In one embodiment, the pyrrolidinophenone compounds to be detected or determined are one or more of the group comprising α-PVP, pyrovalerone, MDPV, MDPBP, naphyrone and MOPVP. In one embodiment, the pyrrolidinophenone compounds to be detected or determined are one or more of the group comprising α-PVP, pyrovalerone and MDPV. The methods of the present invention can be used by employers to identify drugged employees and by law enforcement to identify those who are driving under the influence of drugs. The methods of the present invention can also be used by customs officials to test shipments being imported into a country for drugs.

In one embodiment, the present invention is a method of detecting or determining a compound comprising structure II, IIa or IIb:

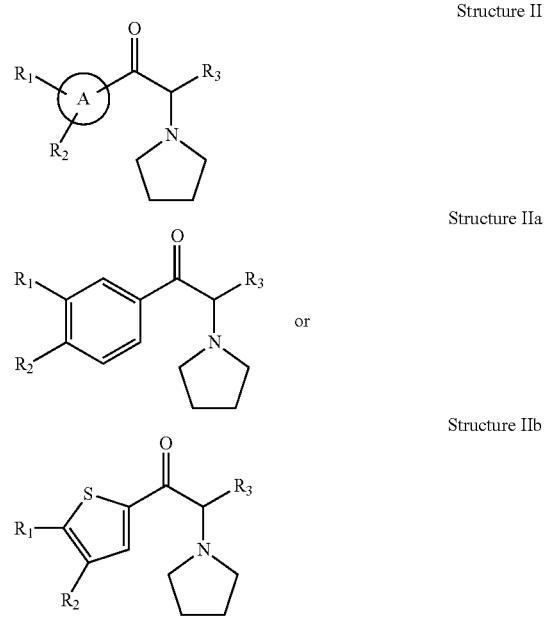

Structure II

Structure IIa or

Structure IIb

Wherein A is aryl; or A is phenyl or thiophene, $R_3$ is $C_1$-$C_6$ alkyl; and each $R_1$ and $R_2$ are independently —H, $C_1$-$C_4$ alkyl, $C_1$-$C_4$ alkoxy, hydroxy substituted $C_1$-$C_4$ alkyl, carboxy, halo, or hydroxy; or $R_1$ and $R_2$ join together to form an optionally substituted:

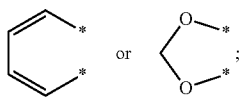

in a sample, the method comprising: i) contacting the sample with a detecting agent and an antibody, wherein the antibody is raisable from an immunogen of structure I:

Structure I

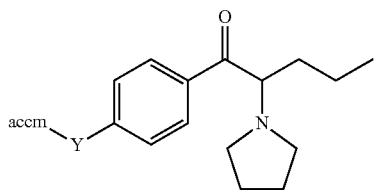

wherein: Y is a crosslinking group; and accm is an antigenicity-conferring carrier material; wherein both the compound and the detecting agent bind to the antibody; and ii) detecting or determining the amount of detecting agent bound to the antibody.

The term "subject" refers to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In another embodiment, the subject is a "human".

For the purposes of the invention, the sample to be used for in vitro analysis can be any sample from which a pyrrolidinophenone compound can be detected, for example hair or a biological sample. The term "biological sample", as used herein, includes, without limitation, cell cultures or extracts thereof; biopsied material obtained from a mammal or extracts thereof; blood, saliva, urine, faeces, semen, tears, or other body fluids or extracts thereof. In one embodiment, the biological sample is a peripheral biological fluid, including whole blood, serum, plasma, or urine. The sample may also be a solution which is suspected of containing a drug.

"Detecting" as referred to herein means qualitatively analysing for the presence or absence of a substance, while "determining" means quantitatively analysing for the amount of a substance. The "detecting agent" is a small molecule (generally of similar structure to a molecule to be detected), which is conjugated to a labelling agent that is able to bind to one of the antibodies of the invention. Alternative names for the "detecting agent" are the "conjugate" or "tracer". The labelling agent is selected from an enzyme, a luminescent substance, a radioactive substance, or a mixture thereof. In one embodiment, the labelling agent is an enzyme, for example a peroxidase, specifically horseradish peroxidase (HRP). Alternatively, or additionally, the labelling agent is a luminescent substance which may be a bioluminescent, chemiluminescent or a fluorescent material. In one embodiment, for the immunoassay method of the invention, the detecting agent is based on a compound with a substituted-cathinone substructure conjugated to an enzyme or fluorescent molecule. The detection method is preferably an ELISA but any suitable immunoassay method may be used, for example, a radioimmunoassay, magnetic immunoassay or a lateral flow test. The antibody can be attached to a solid support, for example, a biochip.

In one embodiment, the detection methods of the present invention may be used to determine if samples or solutions contain pyrrolidinophenone compound of structures II, IIa or IIb. In these instances, the detection methods of the invention can be used as a rapid mechanism to determine if further analysis needs to be conducted to determine if these samples or solutions can be imported into an individual country.

In one embodiment, the detection methods of the present invention may be used to determine the presence and/or quantity of pyrrolidinophenone compound of structure II, IIa or IIb in a subject's hair or bodily fluids. Once the presence and/or quantity of the pyrrolidinophenone compound has been determined, this data can then be used to decide what types of medical treatments may be necessary, including deciding levels of medical monitoring and attention to address the specific symptoms of the subject; deciding on medication to alleviate the physical as well as emotional symptoms of the subject; deciding on medications to decrease withdrawal symptoms; deciding on whether the subject may be able to be maintained in an outpatient treatment program or may need the higher level of structure, guidance, and monitoring provided in an inpatient drug-treatment centre.

One advantage of the methods of the present invention is the speed at which the pyrrolidinophenone compounds can be detected or determined. In one embodiment, the pyrrolidinophenone compound of structure II, IIa or IIb can be detected or determined using the methods of the present invention in between about 2 hours and about 10 minutes, between about 1 hour and about half an hour. In one embodiment, the pyrrolidinophenone compound can be detected or determined using the methods of the present invention in about 30 minutes.

This rapid detection can allow for early treatment of the subject or rapid determination of the legal status of a solution or sample.

In one embodiment, the detection methods of the present invention may be used to determine if samples or solutions contain pyrrolidinophenone compound of structures II, IIa or IIb. In these instances, the detection methods of the invention can be used as a rapid mechanism to determine if further analysis needs to be conducted to determine if these samples or solutions can be imported into an individual country. In one embodiment, the methods of the present invention can be used in employee drug testing, law enforcement including drug driving, and customs officials, for example, to test for shipments to be seized.

In one embodiment, the tracer, conjugate or detecting agent (the terms as used herein are synonymous) used in the immunoassays of the current invention is of the structure:

Structure III

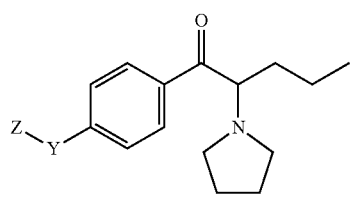

In which Y is a crosslinking group and Z is a labelling agent which is detectable.

Optionally, Y is -(A)$_n$-B-D, in which B is a $C_1$-$C_{10}$, or a $C_1$-$C_6$ optionally substituted alkylene moiety wherein the alkylene optionally incorporates a cycloalkyl and/or a heterocyclic moiety; n=0 or 1 and A is a functional group or heteroatom enabling attachment of the crosslinking group to the phenyl ring and D is a functional group or heteroatom enabling attachment of the crosslinking group to the labelling agent. The term "functional group" is a standard phrase in the chemistry field and refers to a reactive group such as an amine, ketone, ether, thioether, amide, the double bond of an alkene, thiol, ester, carboxylic acid or aldehyde. In one embodiment, A is —O—, —S— or —N—. In another embodiment, A is —O—, —S— or —NH. The substituents of the alkylene chain of B can either be incorporated off, within or at the end of the chain. Usually the substituents will be functional groups at the end of the chain which have participated in chemical bonding in order to from a link between the pyrrolidinophenone structure and the labelling agent. The conjugation of the labelling agent to Y can be facilitated by, for example, the presence of a carboxylic acid or an ester thereof, an aldehyde, an amino group, a maleimide, a halocarboxylic acid or an ester thereof, a dithiopyridyl moiety, a vinylsulphone moiety, a thiocarboxylic acid or an ester thereof. In one embodiment, D is —C(O)—, —NH—, —C═, —C(O)—NH—, —C(O)NH—CH(COOH)—CH$_2$—CH$_2$—S—, —C(O)—NHCH(COOH)—CH$_2$—CH$_2$—S-maleimide-, or —S—. In one embodiment, D is carbonyl, amino, thiol, or diazo. In another embodiment D is —C(O)—, —C(O)—NH—, —NHC(O)—, —NH—, —C═, or —S—. In one embodiment, D is —C(O)—, —NH—, —C(O)—NH—, or —NHC(O)—. In one embodiment D is —C(O)—. In one embodiment, A is —O—, D is —C(O)—, —C(O)NH—CH(COOH)—CH$_2$—CH$_2$—S—, —C(O)—NHCH(COOH)—CH$_2$—CH$_2$—S-maleimide-B is a methylene, and n is 1.

According to another aspect of the invention, there is provided a hapten having the general formula:

Structure IV

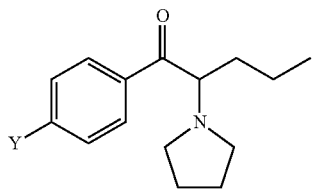

In one embodiment, Y is a crosslinking group. In one embodiment, Y is -(A)$_n$-B-D, in which B is an optionally substituted $C_1$-$C_{10}$ alkylene moiety or an optionally substituted $C_1$-$C_6$ alkylene moiety, wherein the alkylene moieties optionally incorporate a cycloalkyl and/or a heterocyclic moiety; n=0 or 1 and A is a functional group or heteroatom enabling, when present, attachment of the crosslinking group to the phenyl ring and D is a functional group or heteroatom. D can be —CHO, —C(O)NH$_2$, —NHC(O)H, —NH$_2$, —CO$_2$H, —CO$_2$Me, —CO$_2$Et, —CO$_2$Pr, —CO$_2$isoPr, —CO$_2$But, —CO$_2$isoBut, —CO$_2$tertBut, —OH, —C(O)—NH-4-butyrothiolactone, or —SH; or be —CHO, —NH$_2$, —CO$_2$H, —CO$_2$Me, —CO$_2$Et, —CO$_2$Pr, —CO$_2$isoPr, —CO$_2$But, —CO$_2$isoBut, —CO$_2$tertBut, —OH, —C(O)—HCTL, —C(O)—NH—CH(COOH)—CH$_2$—CH$_2$—SH, —C(O)—NHCH(COOH)—CH$_2$—S-maleimide or —SH. In one embodiment, A is —O—, —S— or —NH—. The substituents of the alkylene chain of B can either be incorporated off, within or at the end of the alkylene chain. Usually the substituents will be functional groups at the end of the alkylene chain which have participated in chemical bonding in order to form a link between the pyrrolidinophenone structure and the carrier material. In another embodiment, D is —CO$_2$H, —C(O)—HCTL, —C(O)H, —NH$_2$, or —SH. In one embodiment A is —C(O)—, B is methylene, D is —CO$_2$H or —C(O)—HCTL and n is 1. Compounds of structure IV can be linked with accm to form immunogens of the invention.

Examples of haptens of the current invention are 2-(4-(2-(pyrrolidin-1-yl)pentanoyl)phenoxy)acetic acid (Hapten-1) and N-(2-oxotetrahydrothiophen-3-yl)-2-(4-(2-(pyrrolidin-1-yl) pentanoyl)phenoxy)acetamide (Hapten-2). Preparation of haptens of the current invention is shown in Examples 1-5.

As described herein, compounds of the invention may optionally be substituted with one or more substituents, such as illustrated generally below, or as exemplified by particular species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list.

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "alkyl" as used herein means a saturated straight or branched chain hydrocarbon.

The term "alkylene," as used herein, represents a saturated divalent straight or branched chain hydrocarbon group and is exemplified by methylene, ethylene, isopropylene and the like.

The term "cycloalkyl" (or "carbocycle") refers to a monocyclic, bicyclic or polycyclic fused, spiro or bridged cyclic ring (typically a monocyclic $C_3$-$C_8$ hydrocarbon or bicyclic $C_8$-$C_{12}$ hydrocarbon) that is completely saturated and has a single point of attachment to the rest of the molecule, and wherein any individual ring in said bicyclic ring system has 3-8 members. Suitable cycloalkyl groups include, but are not limited to, cyclopropyl, cyclobutyl, cyclopentyl, cyclohexyl, and cycloheptyl.

The term "heterocycle" (or "heterocyclyl", or "heterocyclic" or "non-aromatic heterocycle") as used herein refers to a non-aromatic ring system which can be saturated or contain one or more units of unsaturation, having three to fourteen ring atoms in which one or more ring carbons is replaced by a heteroatom such as, N, S, or O and each ring in the system contains 3 to 8 members. In some embodiments, non-aromatic heterocyclic rings comprise up to three heteroatoms selected from N, S and O within the ring. In other embodiments, non-aromatic heterocyclic rings comprise up to two heteroatoms selected from N, S and O within the ring system. In yet other embodiments, non-aromatic heterocyclic rings comprise up to two heteroatoms selected from N and O within the ring system. The term includes monocyclic, bicyclic or polycyclic fused, spiro or bridged heterocyclic ring systems. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl.

The term "aryl" (or "aryl ring" or "aryl group") used alone or as part of a larger moiety as in "aralkyl", "aralkoxy", "aryloxyalkyl", or "heteroaryl" refers to both carbocyclic or heterocyclic aromatic ring systems. The term "aryl" may be used interchangeably with the terms "aryl ring" or "aryl group".

"Carbocyclic aromatic ring" groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring" or "carbocyclic aromatic", as it is used herein, is a group in which an aromatic ring is "fused" to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The terms "heteroaryl", "heteroaromatic", "heteroaryl ring", "heteroaryl group", "aromatic heterocycle" or "heteroaromatic group", used alone or as part of a larger moiety as in "heteroaralkyl" or "heteroarylalkoxy", refer to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is "fused" to one or more non-aromatic rings (carbocyclic or heterocyclic), where the radical or point of attachment is on the aromatic ring.

Bicyclic 6.5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "heteroatom" means one or more of oxygen, sulphur, nitrogen, or phosphorus, including any oxidized form of nitrogen, sulphur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR+ (as in N-substituted pyrrolidinyl).

The term "unsaturated," as used herein, means that a moiety has one or more units of unsaturation.

As used herein, a "carboxy" or "carboxylic acid" group refers to —COOH, —OC(O)H, when a terminal group; or —OC(O)— or —C(O)O— when an internal group.

The term "hydroxyl" or "hydroxy" or "alcohol moiety" refers to —OH.

The term "alkoxy," as used herein, refers to an alkyl group, as previously defined, attached to the principal carbon chain through an oxygen atom.

The terms "γ-thiobutyrolactone" and "4-butyrothiolactone" as used herein refers to:

The "2-amino-4-mercaptobutyric acid 1,4-thiolactone", and "homocysteine thiolactone (HCTL)" and as used herein refer to:

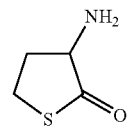

Suitable substituents on a saturated or unsaturated carbon of an alkyl, aryl cycloalkyl, or heterocyclic ring are $C_1$-$C_6$ alkyl, halogen, cyano, oxo, —NCO, —$OR^b$, —$SR^b$, —S(O)$R^a$, —$SO_2R^a$, —$NR^bR^c$, —C(O)$R^b$, —C(O)$OR^b$, —OC(O)$R^b$, —NRC(O)$R^b$, —C(O)$NR^bR^c$, —$NR^bC(O)NR^bR^c$, —$NR^bC(O)OR^b$, —$OCONR^bR^c$, —$C(O)NRCO2R^b$, —$NR^bC(O)NR^bC(O)OR^b$, —C(O)NR($OR^b$), —$SO_2NR^b$, —$NR^bSO_2R^b$, —$NR^bSO_2NR^cR^b$, or —P(O)($OR^a$)$_2$—; or two substituents join together with the atoms to which they are attached to form a 5-7-membered cycloalkyl or heterocyclic ring.

Each $R^a$, $R^b$ and $R^c$ are each independently —H or $C_1$-$C_6$ alkyl.

Other suitable substituents for a saturated carbon of an alkyl, carbocyclic or heterocyclic ring include the following: =O, =S, =NNHR*, =NN(R*)2, =NNHC(O)R*, =NNHCO$_2$(alkyl), =NNHSO$_2$(alkyl), or =NR*, wherein each R* is independently selected from —H or C$_1$-C$_6$ alkyl.

In some embodiments, suitable substituents on the nitrogen of a heteroaryl or heterocyclic ring include those listed above for carbon atoms. Other suitable substituents include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is —H or C$_1$-C$_6$ alkyl.

Nitrogen containing rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Nitrogen containing rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this invention, unless only one of the isomers is drawn specifically. As would be understood to one skilled in the art, a substituent can freely rotate around any rotatable bonds. Therefore, single stereochemical isomers as well as enantiomeric, diastereomeric, cis/trans, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, especially deuterium analogues, can also be therapeutically useful.

The compounds of the invention are defined herein by their chemical structures and/or chemical names. Where a compound is referred to by both a chemical structure and a chemical name, and the chemical structure and chemical name conflict, the chemical structure is determinative of the compound's identity.

In one embodiment, the labelling agent is horseradish peroxidase (HRP). Other conventional labelling agents may be used selected from an enzyme, such as peroxidase, a luminescent substance, a radioactive substance or a mixture thereof.

An example of a conjugate or detecting agent of the current invention is 2-(4-(2-(pyrrolidin-1-yl)pentanoyl)phenoxy)acetic acid (Hapten-1) coupled to HRP. The preparation of this conjugate is shown in Example 8.

The invention further describes a substrate with which the antibodies of the invention engage. The antibodies can engage with the substrate by, for example, passive adsorption or can be chemically bonded to the substrate attached by way of, for example, covalent bonds. Such covalent bonding generally requires the initial introduction of a chemically active compound covalently attached to the substrate surface prior to antibody addition. The antibody itself may also require the addition of a chemical activating group to achieve substrate bonding. These requirements are well known in the art. The substrate can be any medium capable of adsorbing or bonding to an antibody, for example a bead or nanoparticle (optionally chemically-activated), but is preferably of a planar conformation (optionally chemically-activated) such as a microtitre plate (as in Example 9 below) or a biochip. Microtitre plates commonly consist of 6, 24, 96, 384 or 1536 sample wells arranged in a 2:3 rectangular matrix. 96 well microtitre plates are commonly used in an ELISA. A biochip is a thin, wafer-like substrate with a planar surface which can be made of any suitable material such as glass or plastic but is preferably made of ceramic. The biochip is able to be chemically-activated prior to antibody bonding or is amenable to the passive adsorption of antibodies. The skilled person in biochip development for immunoassay application will recognize that a planar surface at high resolution e.g. if using a scanning electron microscope (SEM), is not perfectly "flat" but will possess an uneven surface, the important aspect being that the "approximately" planar surface is suitable for application. A microlayer coating of material can optionally be added to the planar surface of the substrate prior to antibody immobilisation. Either the upper surface or both surfaces of the substrate can be coated.

Enzyme Immunoassays, ELISAs

The enzyme-linked immunosorbent assay (ELISA) is a test that uses antibodies and colour change to identify a substance.

Antigens from the sample are attached to a surface. Then, a further specific antibody is applied over the surface so it can bind to the antigen. This antibody is linked to an enzyme, and, in the final step, a substance containing the enzyme's substrate is added. The subsequent reaction produces a detectable signal, most commonly a colour change in the substrate.

Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed to remove any proteins or antibodies that are not specifically bound. After the final wash step, the plate is developed by adding an enzymatic substrate to produce a visible signal, which indicates the quantity of antigen in the sample.

Lateral Flow Devices

In recent years, the in vitro diagnostics industry has made enormous efforts to develop immunochromatographic tests. Such tests have found applications in both clinical and non-clinical fields. A clinical utility of this test format is particularly suited to point of care utilities.

Rapid immunochromatographic test devices, e.g. in the form of a test strip, are made up of a number of components. Such a test strip commonly includes a sample pad, a conjugate pad, a membrane, e.g. a nitrocellulose membrane, and an absorbent pad. The membrane is usually attached by means of an adhesive to a supporting backing, e.g. made of plastic. In practice, the user dispenses a patient sample (such as urine or whole blood) onto the sample pad. The sample then flows through the sample pad into the conjugate pad, where it mixes with, and releases, the detector reagent. This mixture then flows across the membrane, where it binds with the test and control reagents located in the capture test zone (sample zone) and negative control zone, respectively. When the mixture binds to the reagent that forms the test line, a positive result is indicated. The colour intensity of the test line is proportional to the concentration of analyte in the sample. Excess sample that flows beyond the test and control zones is taken up in the absorbent pad.

Rapid immunochromatographic test devices for diagnostic purposes are easy to operate and thus do not only contribute to the comfort of professional users, e.g. medical stuff, but also allow the operation by non-professional users, e.g. most patients.

Biochips

Biochips are components used for example in chemical analysis (including Proteomic and Molecular analysis) either to host a test reaction and/or to supply samples under test or reagents. Generally, a Biochip comprises a solid substrate, on which is arranged one or more test sites at which a reaction can take place in use. For instance, the test site may carry one or more reagents (e.g. ligands such as antibodies or antigens) adsorbed to the substrate, which are activated by the addition of a sample substance (e.g. analytes present in the sample bind to specific ligands). Such chips are sometimes referred to as a "lab on a chip" and can also incorporate tools for controlling steps of a reaction. As an example, one Biochip supplied by Randox Laboratories Limited (55 Diamond Road, Crumlin, County Antrim, United Kingdom, BT29 4QY) is used as a medium for performing multiplex analysis of biological samples using a chemiluminescence method. In this example, the Biochip takes the form of a small ceramic chip with a specialised surface preparation which is sensitive to environmental degradation. Therefore the Biochip is generally delivered in an environmentally sealed format, usually evacuated, sealed foil bags.

For instance, the Evidence™ analyser by Randox Laboratories Ltd uses biochips which are fitted into a plastic holder defining three recesses arranged in a line. Each recess is approximately square and sized to just accommodate a biochip, which is also square, with a small clearance to allow the chip to be placed. The "strip" of three mounted biochips is placed within a sealed foil bag for storage, which is then opened when the biochips are required for use. The plastic holder may be placed on a carrier alongside two further strips of three biochips to form a 3×3 array of biochips. The carrier has a keying feature for engagement with a robotic arm such that the array can be transported within the analyser via robotic handling. This configuration is useful for batch analysis.

A "Biochip" is a general term for a reaction platform for hosting chemical, biochemical, proteomic or molecular tests, as may be required for medical diagnosis, drug detection, etc. Typically, a Biochip comprises an inert substrate, such as silicon or glass (often of the order of about 1 cm$^2$ or less in surface area), on which one or a plurality of reaction sites is provided. The sites generally carry one or more ligands, for example, one or more antibodies, selected for the test (or "assay") to be performed, adsorbed to the surface of the chip for activation upon combination with a sample applied to the chip (e.g. a blood sample) and/or a reagent. The reactions can be detected using a number of alternative techniques, including detection of chemiluminescence generated by the reaction. Some biochips carry a very large number (hundreds or thousands) of such tests sites, typically arranged in a grid or array, making it possible to carry out numerous assays simultaneously, and using the same single specimen.

General Methodology

Preparation of Haptens, Immunogens and Detecting Agents

Although haptens provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and protein fragments. Illustrative examples of useful carrier materials are bovine serum albumin (BSA), egg ovalbumin (OVA), bovine gamma globulin (BGG), bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof. Immunogen formation for the invention described herein involves conventional conjugation chemistry. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOFMS).

General Procedure for MALDI-TOF Analysis of Immunogens.

MALDI-TOF mass spectrometry can be performed using a Voyager STR Biospectrometry Research Station laser-desorption mass spectrometer coupled with delayed extraction. An aliquot of each sample to be analysed can be diluted in 0.1% aqueous trifluoroacetic acid (TFA) to create 1 mg/ml sample solutions. Aliquots (1 µl) can be analysed using a matrix of sinapinic acid and bovine serum albumin (Fluka) as an external calibrant.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunizing an animal, for example, a mammalian animal, by repeated administration of an immunogen. The serum from the immunized animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal antibodies.

This can be carried out using an ELISA based format as described above for measuring antibody titre or as a Biochip based format. Details of how the antibodies are fixed to the Biochip are described in FitzGerald, S. P. et al, Clin. Chem. 51(7); 1165-1176; 2005. The signal emitted in the immunoassay is proportionate to the amount of detecting agent bound to the antibodies which in turn is inversely proportionate to the analyte concentration. The signal can be detected or quantified by comparison with a calibrator.

STATEMENTS OF THE INVENTION

1) In one embodiment the invention is an immunogen of structure I:

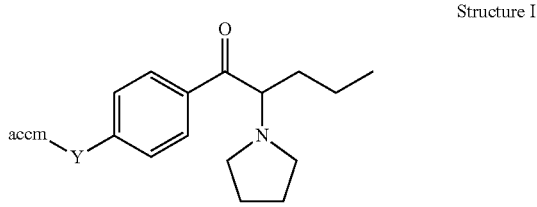

Structure I

In which Y is a crosslinking group and accm is an antigenicity-conferring carrier material.

2) In one embodiment the invention is the immunogen of Statement 1 in which Y is $-(A)_n$-B-D- in which B is a $C_{1-10}$, substituted or unsubstituted alkylene moiety optionally incorporating a cycloalkyl and/or a heterocyclic moiety; n=0 or 1 and A is a functional group or heteroatom enabling attachment of the crosslinker to the phenyl ring and D is a functional group or heteroatom enabling attachment of the crosslinker to the antigenicity-conferring carrier material.

3) In one embodiment the invention is the immunogen of Statement 2 wherein B is a $C_1$-$C_6$ substituted or unsubstituted alkylene moiety.

4) In one embodiment the invention is the immunogen of Statement 2 or 3 wherein n=1, A is O, N or S and D is —C(O)—, —NH—, —C≡, or —S—.

5) In one embodiment the invention is the immunogen of any previous Statement wherein the accm is selected from the group consisting of bovine thyroglobulin, bovine serum albumin, keyhole limpet haemocyanin, bovine gamma globulin and egg ovalbumin.

6) In one embodiment the invention is an antibody which is derived from an immunogen of Statements 1-5 and that binds to an epitope of structure IIa:

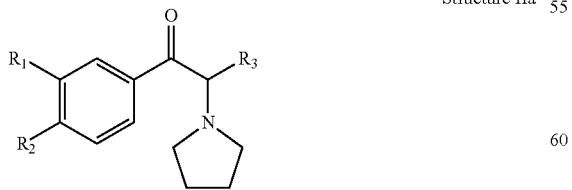

Structure IIa

Wherein $R_3$ is $C_2$-$C_6$ alkyl, $R_1$ and $R_2$ are H, $C_1$-$C_4$ alkyl, $C_1$-$C_4$ alkoxy, hydroxy substituted $C_1$-$C_4$ alkyl, carboxy or hydroxyl, or together form substituted or unsubstituted:

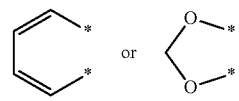

7) In one embodiment the invention is the antibody of Statement 6 which has 100% cross-reactivity to Alpha-PVP and greater than 100% cross-reactivity to Pyrovalerone, MDPV, Naphyrone and 4-Methoxy-alpha-pyrrolidinopentiophenone.

8) In one embodiment the invention is the antibody of Statement 6 or 7 having an $IC_{50}$ of less than about 1 ng/ml for each of Alpha-PVP, Pyrovalerone, MDPV, Naphyrone and 4-Methoxy-alpha-pyrrolidinopentiophenone.

9) In one embodiment the invention is a method of detecting or determining a compound comprising structure IIa in an in vitro sample or in a solution comprising contacting the sample or solution with a detecting agent and an antibody of Statement 6, detecting the bound conjugate and deducing the presence of a compound comprising structure IIa.

10) In one embodiment the invention is the method of Statement 9 wherein the compounds to be detected include one or more of Alpha-PVP, Pyrovalerone, MDPV, Naphyrone and 4-Methoxy-alpha-pyrrolidinopentiophenone.

11) In one embodiment the invention is a kit comprising an antibody of any of Statements 6 to 8.

12) In one embodiment the invention is the kit of claim 11 wherein the antibody is adsorbed on or attached to a solid state device.

13) In one embodiment the invention is the kit of claim 12 wherein the solid state device is a ceramic biochip.

EXAMPLES

Figure 2:
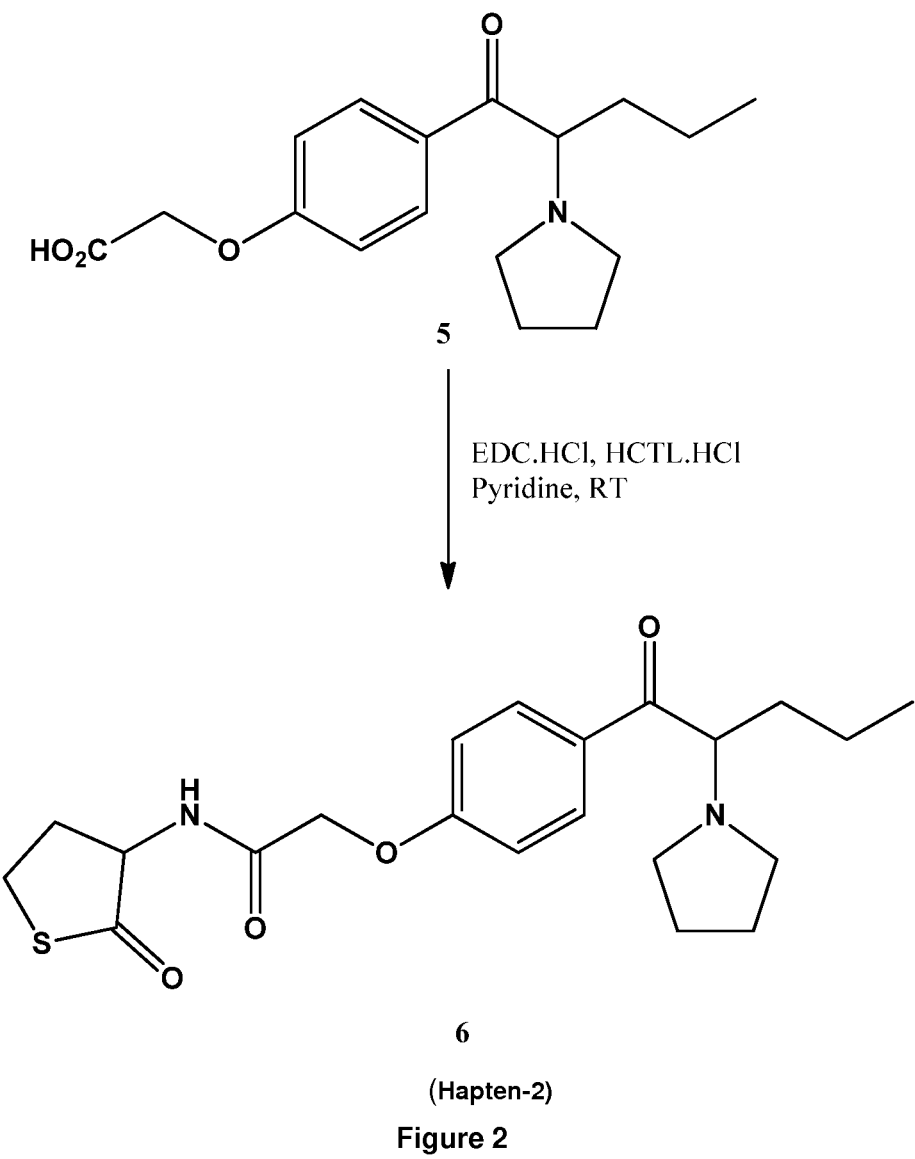
FIG. 2 Synthesis of PVP 4-CME-HCTL 6 (Hapten-2)
FIG. 3 Chemical Structures of Hapten-1 and Hapten-2
FIG. 4 Calibration curve showing absorbance at 450 nm using α-PVP as the standard in an ELISA incorporating antiserum raised from Immunogen-1B.
Figure 3:
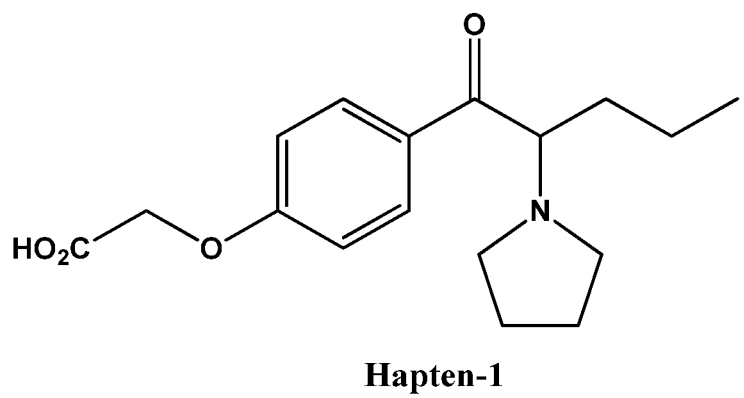
Figure 3:
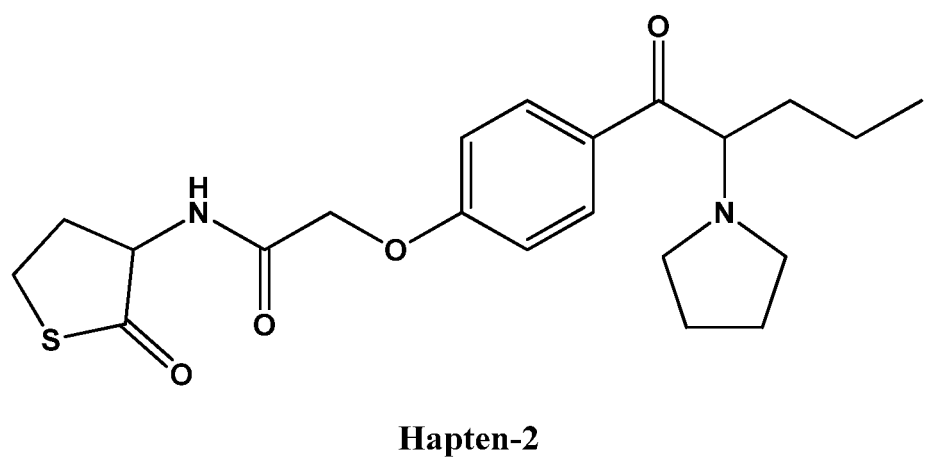
Figure 4:
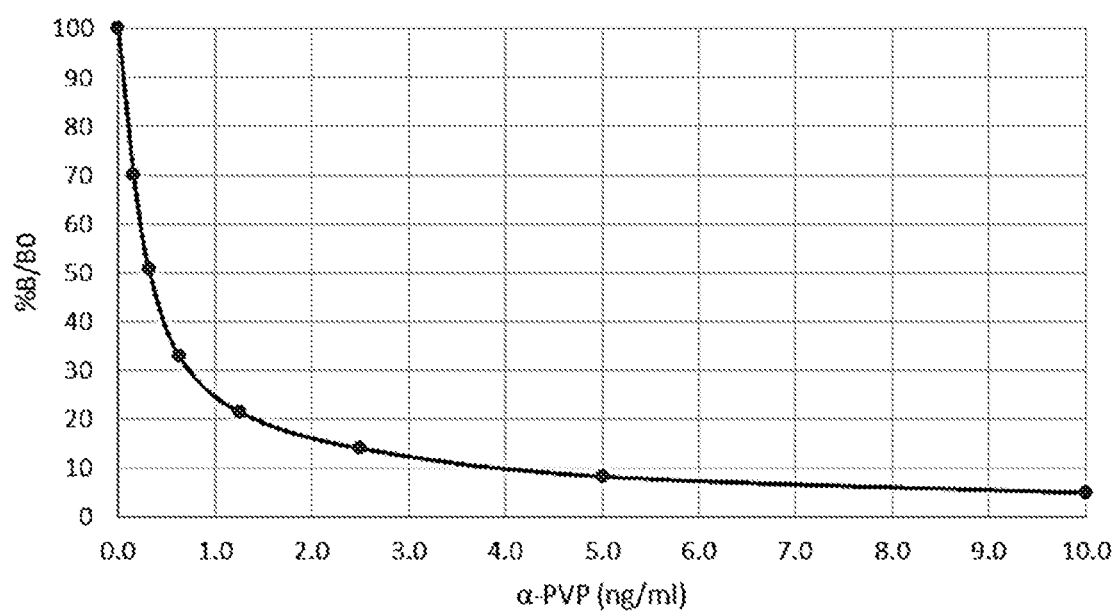

Numbers in (bold) refer to structures in FIGS. 1 and 2.

Example 1: Synthesis of 2-bromo-1-(4-hydroxyphenyl) pentan-1-one (2)

A solution of 4-hydroxyvalerophenone (1) (15 g, 0.084 mol) in acetic acid (100 ml) was added drop-wise to a solution of bromine (4.5 ml, 0.088 mol) in acetic acid (120 ml) at room temperature. The reaction mixture was stirred overnight at room temperature. The solvents were removed under vacuum and the resulting residue was dissolved in water and ethyl acetate. The organic layer was separated, washed with sodium thiosulfate, water and brine. The organic phase was then dried over sodium sulphate, filtered and evaporated to dryness to give 2-bromo-1-(4-hydroxyphenyl)pentan-1-one (2) (25.59 g) as a yellow oil.

Example 2: Synthesis of 1-(4-hydroxyphenyl)-2-(pyrrolidin-1-yl) pentan-1-one.HCl (4-Hydroxy-PVP HCl) (3)

Pyrrolidine (14 ml, 0.168 mol) was added slowly to a solution of 2-bromo-1-(4-hydroxyphenyl) pentan-1-one (2) (25.59 g, 0.084 mol) followed by the addition of potassium carbonate (23.22 g, 0.168 mol). The mixture was stirred at room temperature overnight. The reaction mixture was filtered and the filtrate was evaporated to dryness. The residue was purified by column chromatography (silica gel, 50-100% ethyl acetate in petroleum ether) to give the free base of 1-(4-hydroxyphenyl)-2-(pyrrolidin-1-yl) pentan-1-one (4-OH-PVP) (14.18 g) as an oil. The resulting oil was dissolved in 100 ml methanol and a solution of 2M HCl in ether was added slowly. A precipitate formed was collected by filtration, washed with ether and dried under vacuo to give 1-(4-hydroxyphenyl)-2-(pyrrolidin-1-yl) pentan-1-one.HCl (3) (11.44 g) as a white solid.

Example 3: Synthesis of tert-butyl 2-(4-(2-(pyrrolidin-1-yl)pentanoyl)phenoxy)acetate (4)

Potassium carbonate (2.511 g, 0.0182 mol) was added to a suspension of 1-(4-hydroxyphenyl)-2-(pyrrolidin-1-yl)pentan-1-one.HCl (3) (1.5 g, 5.28 mmol) in tetrahydrofuran (40 ml). To the suspension resulted was added dimethylformamide (10 ml) and the mixture was stirred and heated at 60° C. for 30 min. Tert-butylbromoacetate (2.686 ml, 0.0182 mol) was added and the reaction mixture was stirred at 60-70° C. for 2 hours. The solvent was removed under vacuo and the residue was dissolved in water and ethyl acetate. The organic layer was separated, washed with water, brine, then dried over sodium sulphate, filtered and evaporated to dryness. The resulting oil was purified by column chromatography (silica gel, 10% methanol in dichloromethane) to give tert-butyl 2-(4-(2-(pyrrolidin-1-yl) pentanoyl) phenoxy) acetate (4) (1.37 g) as a yellow oil.

Example 4: Synthesis of 2-(4-(2-(pyrrolidin-1-yl)pentanoyl)phenoxy)acetic acid (PVP 4-CME) (5) (Hapten-1)

Trifluoroacetic acid (10 ml) was added to a solution of tert-butyl 2-(4-(2-(pyrrolidin-1-yl) pentanoyl) phenoxy) acetate (4) (1.37 g, 3.79 mmol) in dichloromethane (20 ml) at 0° C. The solution was allowed to warm-up to room temperature and stirred for 2 hours. The solvent was removed in vacuo to give a light brown foamy solid. The residue was purified by column chromatography (silica gel, 10% MeOH in ethyl acetate) to give 2-(4-(2-(pyrrolidin-1-yl)pentanoyl)phenoxy)acetic acid (PVP 4-CME) (5) (Hapten-1) (596 mg) as a foamy oil.

NMR 13C (CD3OD): 194.27, 170.67, 164.10, 161.6, 131.53 (2), 127.97, 155.36 (2), 69.98, 64.82, 55.21, 52.35, 32.88, 23.02, 17.48, 13.23.

Example 5: Synthesis of N-(2-oxotetrahydrothiophen-3-yl)-2-(4-(2-(pyrrolidin-1-yl) pentanoyl)phenoxy)acetamide (PVP 4-CME HCTL) (Hapten-2) (6)

D,L-Homocysteine thiolactone hydrochloride (60.43 mg, 0.39 mmol) and EDC.HCl (75.41 mg, 0.39 mmol) were added to a solution of 2-(4-(2-(pyrrolidin-1-yl)pentanoyl) phenoxy)acetic acid (PVP 4-CME) (5) (Hapten-1) (109 mg, 0.35 mmol) in pyridine (10 ml) at room temperature. The solution was stirred at room temperature overnight. The solvent was removed in vacuo and the residue was dissolved in water and dichloromethane. The organic layer was separated, dried over sodium sulphate, filtered and evaporated to dryness. The residue was purified by column chromatography (silica gel, 10% MeOH in chloroform) to give N-(2-oxotetrahydrothiophen-3-yl)-2-(4-(2-(pyrrolidin-1-yl)pentanoyl)phenoxy)acetamide (PVP 4-CME HCTL) (6) (Hapten-2) (100 mg) as a foamy oil.

Example 6: Conjugation of PVP 4-CME (5) (Hapten-1) to BSA (Immunogen-1A)

To a solution of PVP 4-CME (5) (Hapten-1) (23.5 mg) in DMF (1.0 ml) was added N-(3-Dimethylaminopropyl)-N'-ethylcarbodiimide hydrochloride EDC.HCl (73.7 mg) and N-hydroxysuccinimide (44.3 mg) and the mixture was incubated on the roller at room temperature overnight. This solution was added drop-wise to a solution of BSA (100 mg, 1.5 mmol) in phosphate buffer saline (50 mM) (pH 8.0) (10 ml). The resulting solution was incubated on the roller at room temperature overnight. Excess hapten was removed by dialysis against phosphate buffer saline, pH 7.2 (3 changes) for 24 hours at 4° C., and freeze-dried.

MALDI results showed 19.8 molecule of PVP 4-CME (Hapten-1) had been conjugated to one molecule of BSA.

Example 7: Conjugation of PVP 4-CME (5) (Hapten-1) to KLH (Immunogen-1B)

To a solution of PVP 4-CME (Hapten-1) (5) (27.7 mg) in DMF (1.0 ml) was added N-(3-Dimethylaminopropyl)-N'-ethylcarbodiimide hydrochloride (EDC.HCl) (73.7 mg) and N-hydroxysuccinimide (44.3 mg) and the mixture was incubated on the roller at room temperature overnight. This solution was added drop-wise to a solution of KLH (100 mg) in phosphate buffer saline (50 mM) (pH 8.0) (10 ml). The resulting solution was incubated on the roller at room temperature overnight. Excess hapten was removed by dialysis against phosphate buffer saline, pH 7.2 (3 changes) for 24 hours at 4° C., and freeze-dried.

Example 8: Conjugation of PVP 4-CME (Hapten-1) (5) to HRP (Tracer-1)

EDC hydrochloride (1.5 mg) was dissolved in water (0.5 ml) and immediately added to a solution of PVP 4-CME (Hapten-1) (5) (3 mg) in DMF (0.2 ml). After mixing, this solution was added drop-wise to a solution of HRP (20 mg) in water (1 ml). N-hydroxysuccinimide (1 mg) was added and the reaction mixture was incubated in the dark at room temperature overnight. Excess hapten was removed with double PD-10 columns (Pharmacia) in series, pre-equilibrated with PBS at pH 7.2. The Hapten-1-HRP conjugate (Tracer-1) was then dialysed overnight against 10 L of PBS at pH 7.2 at 4° C.

Example 9: Preparation of Antisera

In order to generate polyclonal antisera, 2 mg of an Immunogen-1B of the Example 7 is prepared in PBS, mixed at a ratio of 50% immunogen in PBS with 50% Freund's Complete adjuvant (Sigma, Product Number—F5881) and emulsified by repeatedly passing the mixture through a tip on the end of a 1 ml syringe, until it reaches the required semi-solid consistency. 1 ml of the mixture is then injected into a host animal, such as rabbit, sheep, mouse, guinea pig or horse. In one embodiment, sheep are the host animal. Further injections (boosts) are administered on a monthly basis (1 mg of immunogen is prepared in PBS and mixed at a ratio of 50% immunogen in PBS with 50% of Freund's Incomplete Adjuvant, Sigma product Number—F5506) until the required titre is achieved. Serum is sampled for evaluation of the antibody titre.

Briefly, blood is collected by applying pressure to the exposed jugular vein and inserting a clean 14 gauge hypodermic needle to remove 500 ml of blood per sheep, under gravity. The blood is stored at 37° C. for a minimum of 1 hour before the clots are separated from the side of the centrifuge bottles using disposable 1 ml pipettes (ringing). The samples are stored at 4° C. overnight.

Samples are then centrifuged at 4200 rpm for 30 minutes at 4° C. The serum is poured off and centrifuged again, at 10,000 rpm for 15 minutes at 4° C., before being aliquoted and stored at <−20° C. The Immunoglobulin (Ig) fraction is extracted from the antisera via caprylic acid/ammonium sulphate precipitation of immunoglobulin.

The antibody titre is evaluated by coating a microtitre plate (Thermo Fisher Scientific NUNC, 468667) with antibody (125 μl/well) in coating buffer (10 mM Tris pH 8.5) at 37° C. for 2 hours. The plate is then washed 4 times over 10 minutes with working strength TBST. 50 μl of sample/standard (α-PVP) is added to the appropriate wells in triplicate, followed by 75 μl of hapten-HRP conjugate and incubated at 25° C. for 1 hour. The plate is then washed and 125 μl of tetramethylbenzidine (TMB) substrate (Randox Laboratories, 4380-15) added to each well and left at room temperature for 20 mins in the dark. The reaction is stopped using 125 μl of 0.2 M sulphuric acid. The absorbances are read at 450 nm with an ELISA microplate reader (BIO-TEK Instruments, Elx800) and the means calculated. Antibody sensitivity can then be determined.

When the optimal titre has been attained, the host animal is bled to yield a suitable volume of specific antiserum (overall this results in 20 bleeds in total, with approximately 200 ml of antiserum achieved per bleed). The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Various purification steps are available if required, including Immunoglobulin Precipitation (as described above), Antigen-specific affinity purification, Size-exclusion chromatography and Ion Exchange Chromatography. In the present example, IgG was extracted from the antisera using ammonium sulphate/caprylic acid precipitation, yielding polyclonal Antibody-1B.

Example 10: Development of an Immunoassay for Pyrrolidinophenone Based Compounds The purified polyclonal antibody from Example 9 (Antibody-1B) was immobilised on a 96 well ELISA plate at 2.5 μg/ml in 10 mM TRIS buffer, pH 8.5 overnight at 4° C. The assay is based on competition for binding sites of a polyclonal antibody between HRP tracer (Tracer-1) and α-PVP or potential cross-reactants. The plate was washed (×3) with TBST (Tris-Buffered Saline/Tween solution) and the calibrator (α-PVP) or potential cross reactants added (50 μl per well), followed by HRP tracer (Tracer-1) (75 μl/well) to the appropriate wells. The plates were then incubated for 60 minutes at 25° C. They were then subjected to 2 quick wash cycles using TBST, followed by 4×2 minute wash cycles. 125 μl of signal (TMB) was then added to each well for 20 mins at room temperature in the dark. The reaction was stopped by the addition of 125 μl of 0.2 M sulphuric acid per well and the plates read immediately at 450 nm. Calibration curves were generated using α-PVP and these were used to determine the sensitivity and specificity of the immunoassay for potential cross-reactants. The data was inputted to a computer program called KC Junior (Biotek). It gives a 4 parameter fit curve and allows the calculation of concentrations between the standard runs. This program is used to calculate the $IC_{50}$ values by dividing the 0 ng/ml optical density (OD) value by 2 and obtaining the concentration value from the curve for this OD. The results of this study are presented in Tables 1 and 2, cross-reactivity being calculated according to the following formula:

$$\% \ CR = IC_{50} \ \textit{I-PVP}/IC_{50} \ CR \times 100$$

wherein % CR is the percentage cross-reactivity, $IC_{50}$ α-PVP is the concentration of α-PVP which causes 50% displacement of signal and $IC_{50}$ CR is the concentration of potential cross-reactant that causes 50% displacement of signal.

Antibody-1B (Example 9) used to generate the data in the tables below was raised from Immunogen-1B (Example 7) and the HRP tracer (Tracer-1) was prepared as in Example 8. All of the compounds in Table 2 are commercially available from suppliers such as Cayman Chemical (Ann Arbor, Mich., USA).

TABLE 1

ELISA results for Antibody-1B coated at 2.5 μg/ml with Tracer-1 at a dilution of 1/128k.

| Standard (ng/ml) | Average OD | % CV | $B/B_0$ |
|---|---|---|---|
| 0.000 | 1.583 | 0.7 | 100 |
| 0.156 | 1.109 | 1.4 | 70 |
| 0.313 | 0.805 | 0.8 | 51 |
| 0.625 | 0.521 | 1.6 | 33 |
| 1.250 | 0.339 | 0.8 | 21 |
| 2.500 | 0.221 | 0.0 | 14 |
| 5.000 | 0.130 | 0.0 | 8 |
| 10.000 | 0.077 | 0.9 | 5 |
| $IC_{50}$ | | 0.315 | |

B = absorbance at 450 nm at x ng/ml standard concentration
$B_0$ = absorbance at 450 nm at 0 ng/ml standard concentration
$IC_{50}$ = standard concentration which produces 50% $B/B_0$
OD = Optical density
CV = Coefficient of variation

TABLE 2

Cross-reactivity with other compounds of the pyrrolidinophenone family: Antibody-1B coated at 2.5 μg/ml with Tracer-1 at a dilution of 1/128k.

| Standard | % Cross-reactivity | $IC_{50}$ (ng/ml) |
|---|---|---|
| α-PVP | 100 | 0.315 |
| α-Pyrrolidinopropiophenone | <3.150 | >10 |
| Pyrovalerone | 187.500 | 0.168 |
| MDPV | 178.977 | 0.176 |
| MDPBP | 20.561 | 1.532 |
| (+/−) 4'-Methyl-α-pyrrolidinopropiophenone | <3.150 | >10 |
| Naphyrone | 142.534 | 0.221 |
| 4-Methoxy-α-pyrrolidinopentiophenone | 135.193 | 0.233 |

TABLE 3

Chemical structures of pyrrolidinophenone compounds

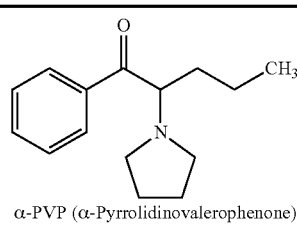

α-PVP (α-Pyrrolidinovalerophenone)

TABLE 3-continued

Chemical structures of pyrrolidinophenone compounds

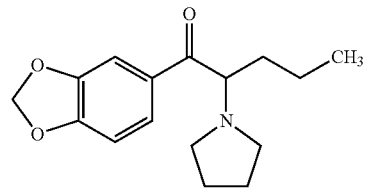 [SMILES: CCCC(C(=O)c1ccc2c(c1)OCO2)N1CCCC1]

MDPV (3',4'-Methylenedioxy-α-pyrrolidinopentiophenone)

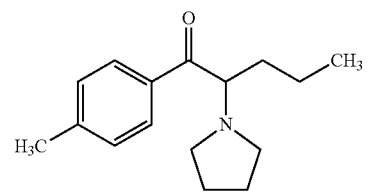 [SMILES: CCCC(C(=O)c1ccc(C)cc1)N1CCCC1]

MPVP (PYROVALERONE) (4-Methyl-α-pyrrolidinopentiophenone)

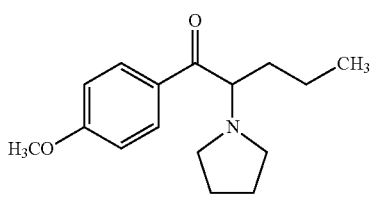 [SMILES: CCCC(C(=O)c1ccc(OC)cc1)N1CCCC1]

MOPVP (4'-Methoxy-α-pyrrolidinopentiophenone)

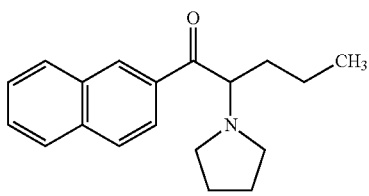 [SMILES: CCCC(C(=O)c1ccc2ccccc2c1)N1CCCC1]

NAPHYRONE

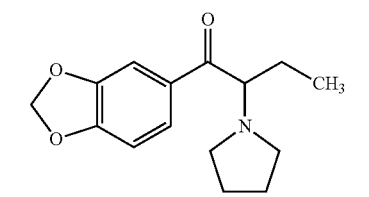 [SMILES: CCC(C(=O)c1ccc2c(c1)OCO2)N1CCCC1]

MDPBP (3',4'-Methylenedioxy-α-pyrrolidinobutiophenone)

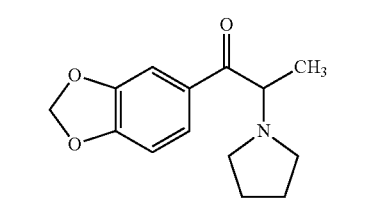 [SMILES: CC(C(=O)c1ccc2c(c1)OCO2)N1CCCC1]

MDPPP (3',4'-Methylenedioxy-α-pyrrolidinopropiophenone)

TABLE 3-continued

Chemical structures of pyrrolidinophenone compounds

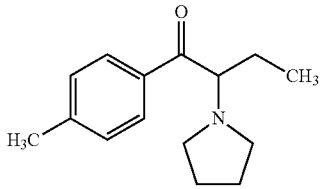 [SMILES: CCC(C(=O)c1ccc(C)cc1)N1CCCC1]

MPBP (4'-Methyl-α-pyrrolidinobutiophenone)

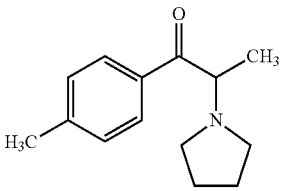 [SMILES: Cc1ccc(C(=O)C(C)N2CCCC2)cc1]

MPPP (4'-Methyl-α-pyrrolidinopropiophenone)

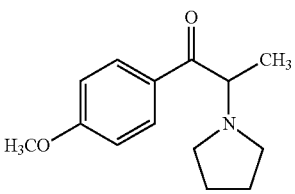 [SMILES: COc1ccc(C(=O)C(C)N2CCCC2)cc1]

MOPPP (4'-Methoxy-α-pyrrolidinopropiophenone)

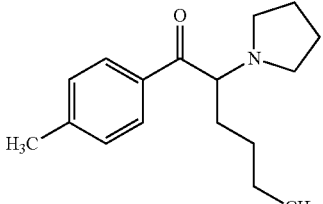

MPHP (4'-Methyl-α-pyrrilidinohexylphenone)

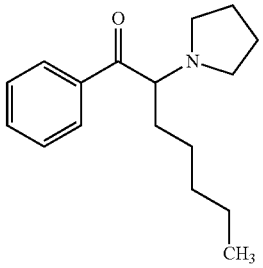 [SMILES: CCCCCC(C(=O)c1ccccc1)N1CCCC1]

α-PHPP (α-Pyrrolidinoheptanophenone)

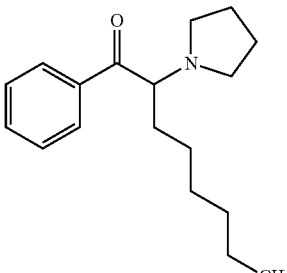

α-POP (α-Pyrridino-octanophenone)

TABLE 3-continued

Chemical structures of pyrrolidinophenone compounds

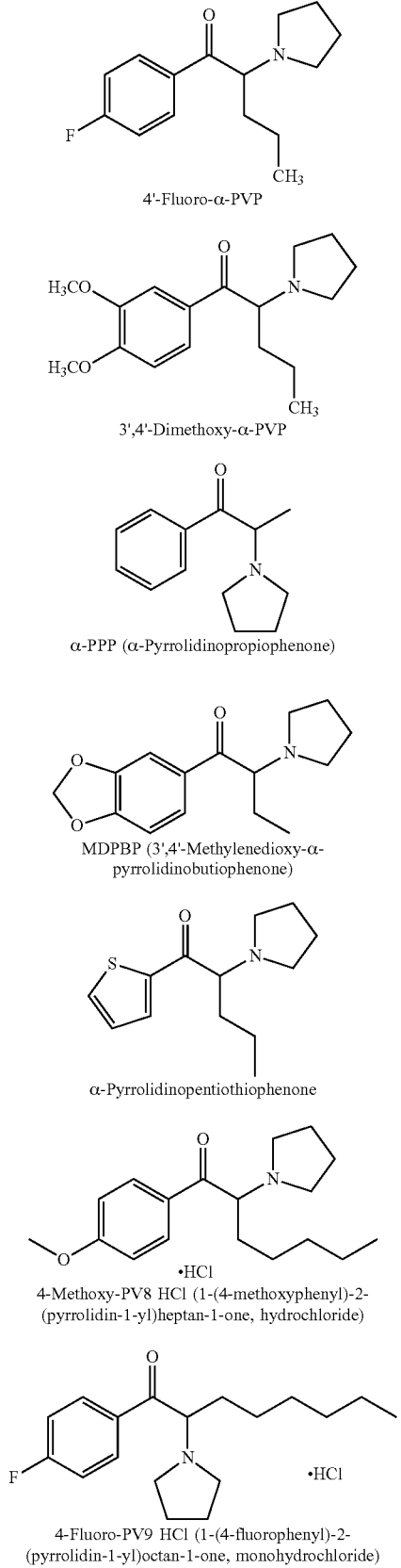

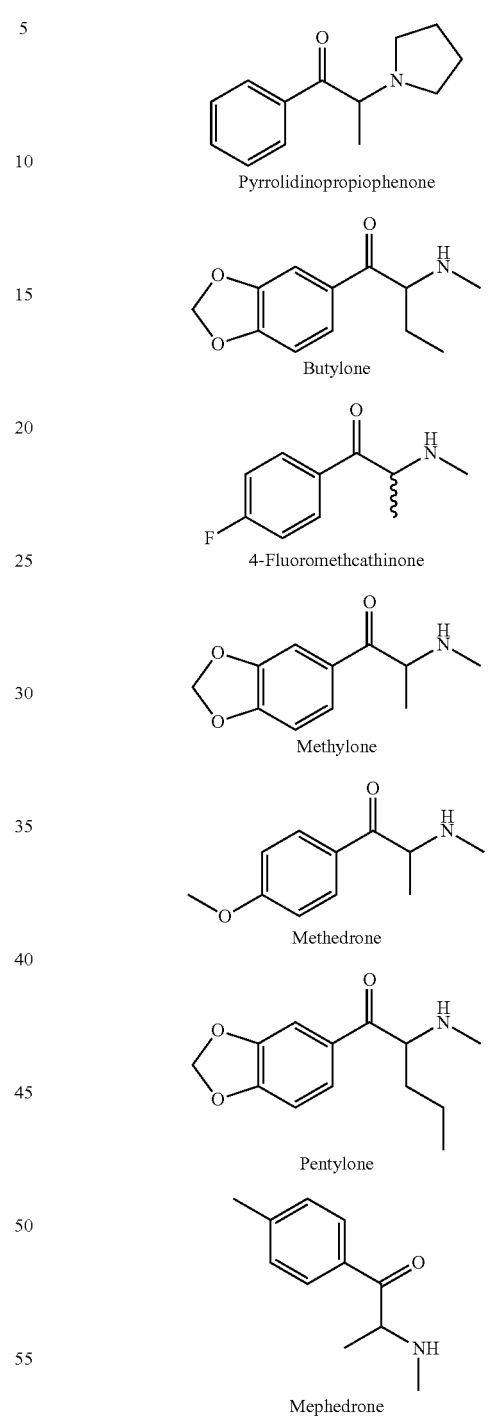

Example 11: Development of an Immunoassay for Pyrrolidinophenone Based Compounds Principle A microtitre plate was precoated with α-PVP antibody. α-PVP (antigen), if present in the sample competes with the horseradish peroxidase labelled α-PVP (enzyme labelled antigen) for a limited number of antibody sites on the microtitre plate. After incubation at room temperature to allow a competition reaction to take place, the microtitre plate was washed to remove excess reagents. The enzyme substrate was added. After an incubation period to allow maximum colour development, the colour reaction was stopped by the addition of acid. This produces a colour change from blue to yellow, and the absorbances are read at 450 nm. A standard curve was then constructed to determine the α-PVP concentration in the sample.

Samples

This kit measured the level of α-PVP in urine and whole blood samples.

Urine Sample Preparation

1. Urine samples were centrifuged at 13000 rpm (9500 RCF) for 60 seconds.
2. Urine samples were diluted 1:50 with diluent (I.e. 10 µl sample+490 µl diluent).
3. The sample was mixed gently by pipetting without the formation of foam.

Whole Blood Sample Preparation

1. Whole blood samples were diluted 1:50 with diluent (i.e. 10 µl sample+490 µL diluent).
2. The sample was mixed gently by pipetting without the formation of foam.

Procedure

All reagents were allowed to reach room temperature (+15° C. to +25° C.) prior to use.

The assay was performed in duplicate. The layout of Table 4 was used where each box represents 2 wells:

TABLE 4

| Assay layout | | | | | |
| --- | --- | --- | --- | --- | --- |
| S1 | T1 | T9 | T17 | T25 | T33 |
| S2 | T2 | T10 | T18 | T26 | T34 |
| S3 | T3 | T11 | T19 | T27 | T35 |
| S4 | T4 | T12 | T20 | T28 | T36 |
| S5 | T5 | T13 | T21 | T29 | T37 |
| S6 | T6 | T14 | T22 | T30 | T38 |
| QC | T7 | T15 | T23 | T31 | T39 |
| QC | T8 | T16 | T24 | T32 | T40 |

S = Standard
QC = Quality Control
T = Test Sample a) Table 5 details what was pipetted into the appropriate wells of the microtitre plate:

TABLE 5

| Assay well contents | | | |
| --- | --- | --- | --- |
| | Standard | Sample | Q.C. |
| Standard | 50 µl | — | — |
| Sample | — | 50 µl | — |
| Q.C. | — | — | 50 µl |
| Conjugate | 75 µl | 75 µl | 75 µl | b) The microtitre plate was gently tapped from side to side for a few seconds.
c) The microtitre plate was covered with a plate sealer before incubating for 30 minutes at room temperature (+15° C. to +25° C.) in the dark.
d) The plate was inverted and the liquid tapped out liquid.
e) The plate was washed 6 times with diluted wash buffer (ensuring all wells were filled), over a 10-15 minute period. After the final wash the liquid was discarded liquid and the plate was tapped onto lint free tissue paper until completely dry.
f) Immediately after washing, one 125 µl shot of substrate was pipetted into each well using a multichannel pipette. The microtitre plate was gently tapped from side to side and incubated for 20±2 minutes at room temperature (+15 to +25° C.) in the dark.
g) The colour reaction was stopped by the addition of 100 µl of stop solution per well. A colour change from blue to yellow resulted.
h) The optical density was measured at 450 nm within 10 minutes of stopping the colour reaction. The use of a 630 nm filter was used as the reference wavelength.

Standard Curve and Interpretation of Results a) The mean absorbance of the standards, controls and samples was calculated.
b) Absorbances of standards against $\log_{10}$ (standard concentration) was plotted.
c) The control and sample concentrations were read from the standard curve.
d) The concentrations for urine samples in ng/ml were calculated by multiplying the results by 50 to take into account the dilution factor.
e) The concentrations for whole blood samples in ng/ml were calculated by multiplying the results by 50 to take into account the dilution factor.
f) A 4 parameter curve fit method was used when generating the standard curve.

Assay Cut-Off

By applying the provided sample dilution for each matrix, the α-PVP/MDPV ELISA Kit achieved the cut-off values indicated in Table 6.

TABLE 6

| Cut-off values | | |
| --- | --- | --- |
| | Urine (ng/ml) | Whole Blood (ng/ml) |
| α-PVP | 20 | 10 |

Assay Range

By applying the provided sample dilution for each matrix, the α-PVP/MDPV ELISA Kit achieved the assay range indicated in Table 7.

TABLE 7

| Assay range | | |
| --- | --- | --- |
| Standard Conc. with no sample dilution applied (ng/ml) | Standard Conc. for Urine Sample with 1:50 dilution (ng/ml) | Standard Conc. for Blood Sample with 1:50 dilution (ng/ml) |
| 0.00 | 0.00 | 0.00 |
| 0.02 | 1.23 | 1.23 |
| 0.07 | 3.70 | 3.70 |
| 0.22 | 11.11 | 11.11 |
| 0.67 | 33.33 | 33.33 |
| 2.00 | 100.00 | 100.00 |

Limits of Detection

TABLE 8

α-PVP limit of detection - Urine

| | Urine (ng/ml) |
|---|---|
| α-PVP | 3.1 |

N = 20 (based on samples diluted 1:50)

TABLE 9

α-PVP limit of detection - Whole Blood

| | Whole Blood (ng/ml) |
|---|---|
| α-PVP | 1.8 |

N = 20 (based on samples diluted 1:50)

Specificity

The specificity of the α-PVP/MDPV ELISA kit is summarised in Table 10.

TABLE

α-PVP/MDPV ELISA kit specificity
Cross-Reactivity of related compounds

| Compound | % Cross-Reactivity |
|---|---|
| Desmethyl Pyrovalerone (α-PVP) | 100 |
| Pyrovalerone | 125.4 |
| 3,4-Methylenedioxypyrovalerone (MDPV) | 93.3 |
| α-Pyrrolidinopentiothiophenone HCl | 73.2 |
| Naphyrone | 70.2 |
| 4-Methyl-α-Pyrrolidinohexanophenone (4-MPHP) | 38.1 |
| 4'-Methyl-α-Pyrrolidinobutiophenone (MPBP) | 23.2 |
| MDPBP HCl | 17.2 |
| 4-Methoxy-PV8 HCl | 11.7 |
| 4-Fluoro-PV9 HCl | 3.2 |
| 4'-Methyl-α-Pyrrolidinopropiophenone HCl | 1.8 |
| 3,4-Methylenedioxy-α-Pyrrolidinopropiophenone (MDPPP) | 0.8 |
| Pyrrolidinopropiophenone | 0.8 |
| Butylone | <1 |
| 4-Fluoromethcathinone | <1 |
| Methylone | <1 |
| Methedrone | <1 |
| Pentylone | <1 |
| Mephedrone | <1 |

TABLE 11

IC50 data for α-PVP/MDPV ELISA kit
$IC_{50}$ data:

| | STD $IC_{50}$[1] | Reactant $IC_{50}$[2] | % CR |
|---|---|---|---|
| α pvp | 0.153 | 0.153 | 100 |
| pyrovalerone | 0.153 | 0.122 | 125.4 |
| mdpv | 0.153 | 0.164 | 93.3 |
| pyrrolidinopentiothiophenone | 0.18 | 0.246 | 73.2 |
| Naphyrone | 0.153 | 0.218 | 70.2 |
| mdpbp | 0.18 | 1.044 | 17.2 |
| mdppp | 0.149 | 17.727 | 0.8 |
| pyrrolidinopropiophenone | 0.149 | 18.744 | 0.8 |

STD = standard (which, in each case, was alpha-pvp).

The different values for STD $IC_{50}$s (i.e. [1] in the table above) are the result of the assays being carried out in separate runs, i.e., when all compounds with STD $IC_{50}$ of 0.153 (for example, a pvp, pyrovalerone, mdpv and naphyrone) were assessed in the same run. Equally, pyrrolidinopentiothiophenone and mdpbp were assessed in the same run; and mdppp and α-pyrrolidinopropiophenone were assessed in the same run. Batches of standards were made leading to variance between them. The Reactant $IC_{50}$s (i.e. [2] in the table above) are the standard concentrations which produced 50% $B/B_0$ in that run. The % CR (last column in the table above) is calculated with reference to the standard used in that particular run.

Precision and Recovery

Typical intra-assay precision is summarised in Table 12.

TABLE 12

Intra assay precision

| Standard (ng/mL) | %B/Bo | Number of replicates | % CV |
|---|---|---|---|
| 0.00 | 100 | 12 | 5.8 |
| 0.02 | 87 | 12 | 4.8 |
| 0.07 | 71 | 12 | 6.1 |
| 0.22 | 43 | 12 | 6.3 |
| 0.67 | 21 | 12 | 6.1 |
| 2.00 | 9 | 12 | 4.3 |

Inter-assay precision and % recovery are summarised in Table 13 and Table 14. Calculated from 3 replicates over 5 runs for 3 samples (50% below cut off, cut off and 50% above cut off).

TABLE 13

Inter-assay precision and % recovery - Urine
Urine

| Concentration (ng/mL) | Mean reported Concentration (ng/ml) | % Recovery | % CV |
|---|---|---|---|
| 10 | 9.86 | 98.6 | 5.4 |
| 20 | 17.20 | 86.0 | 6.1 |
| 30 | 26.52 | 88.4 | 8.5 |

TABLE 14

Inter-assay precision and % recovery - Whole Blood
Whole Blood

| Concentration (ng/mL) | Mean reported Concentration (ng/ml) | % Recovery | % CV |
|---|---|---|---|
| 5 | 4.99 | 99.8 | 4.3 |
| 10 | 9.00 | 90.0 | 6.7 |
| 20 | 16.32 | 81.6 | 6.8 |

Example 11 is a validation assay which has been more refined and also uses calibrators assigned via HPLC which may account for the slight differences in results when comparing Example 10 to Example 11.

The invention claimed is:

1. A polyclonal antibody having 100% cross-reactivity to α-pyrrolidinovalerophenone (α-PVP), greater than 100% cross-reactivity to pyrovalerone, less than 100% but more than 70% cross-reactivity to 3,4-methylenedioxy-α-pyrrolidinopentiophenone (MDPV), α-pyrrolidinopentiothiophenone and naphyrone, and less than 1% cross-reactivity to 3,4-methylenedioxy-α-pyrrolidinopropiophenone (MDPPP), α-pyrrolidinopropiophenone, butylone, 4-fluoromethcathinone, methylone, methedrone, pentylone, and mephedrone, standardized with α-PVP and using Tracer 1, wherein α-PVP is:

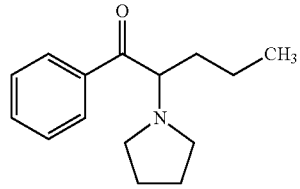 [SMILES: CCCC(C(=O)c1ccccc1)N1CCCC1]

and Tracer 1 is 2-(4-(2-(pyrrolidin-1-yl)pentanoyl)phenoxy)acetic acid (PVP 4-CME)-horseradish peroxidase (HRP).

2. The polyclonal antibody of claim 1, having an IC50 of less than 1 ng/ml for each of α-pyrrolidinovalerophenone (α-PVP), pyrovalerone and 3,4-methylenedioxy-α-pyrrolidinopentiophenone (MDPV).

3. The polyclonal antibody of claim 1, which has been purified.

4. The polyclonal antibody of claim 3, wherein the purification is by immunoglobulin precipitation.

5. The polyclonal antibody of claim 1, wherein the antibody is adsorbed on or attached to a solid state device.

6. A kit comprising the polyclonal antibody of claim 1.

7. The kit of claim 6, wherein the polyclonal antibody is adsorbed on or attached to a solid state device.

* * * * *